United States Patent
Liao et al.

(10) Patent No.: US 11,634,424 B2
(45) Date of Patent: Apr. 25, 2023

(54) DIAZAINDOLE DERIVATIVE AND USE THEREOF AS CHK1 INHIBITOR

(71) Applicant: MEDSHINE DISCOVERY INC., Jiangsu (CN)

(72) Inventors: Yonggang Liao, Shanghai (CN); Wenyuan Qian, Shanghai (CN); Changqing Wei, Shanghai (CN); Yao Xiao, Shanghai (CN); Zhengying Xi, Shanghai (CN); Chen Zhang, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/779,310

(22) PCT Filed: Nov. 27, 2020

(86) PCT No.: PCT/CN2020/132306
§ 371 (c)(1),
(2) Date: May 24, 2022

(87) PCT Pub. No.: WO2021/104461
PCT Pub. Date: Jun. 3, 2021

(65) Prior Publication Data
US 2023/0017858 A1     Jan. 19, 2023

(30) Foreign Application Priority Data

Nov. 29, 2019 (CN) .......................... 201911206315.0
Aug. 7, 2020 (CN) .......................... 202010790385.1

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .............................. C07D 487/04; A61P 35/00
See application file for complete search history.

(56) References Cited

U.S. PATENT DOCUMENTS

| | | | |
|---|---|---|---|
| 10,010,547 B2 | 7/2018 | Boyle et al. | |
| 2021/0137918 A1 | 5/2021 | Cai et al. | |

FOREIGN PATENT DOCUMENTS

| | | | | |
|---|---|---|---|---|
| CN | 102245597 | A | 11/2011 | |
| CN | 106170288 | A | 11/2016 | |
| CN | 108601781 | A | 9/2018 | |
| WO | 2003093297 | A2 | 11/2003 | |
| WO | 2004063198 | A1 | 7/2004 | |
| WO | 2005009435 | A1 | 2/2005 | |
| WO | 2005066163 | A2 | 7/2005 | |
| WO | 2009089042 | A1 | 7/2009 | |
| WO | WO 2009/089042 | * | 7/2009 | ........... C07D 401/14 |
| WO | 2019156438 | A1 | 8/2019 | |
| WO | 2002070494 | A1 | 9/2022 | |

OTHER PUBLICATIONS

Feb. 25, 2021 International Search Report issued in International Patent Application No. PCT/CN2020/132306.
Feb. 25, 2021 Written Opinion of the International Searching Authority issued in International Patent Application No. PCT/CN2020/132306.
Nov. 22, 2022 Japanese First Office Action issued in Japanese Patent Application No. 2022531590.

* cited by examiner

*Primary Examiner* — Erich A Leeser
(74) *Attorney, Agent, or Firm* — Houston Beshining Law Office PLLC; Liangang Ye

(57) ABSTRACT

Disclosed are a diazaindole derivative as shown in formula I and the use thereof in the preparation of a drug for treating Chk1-related diseases.

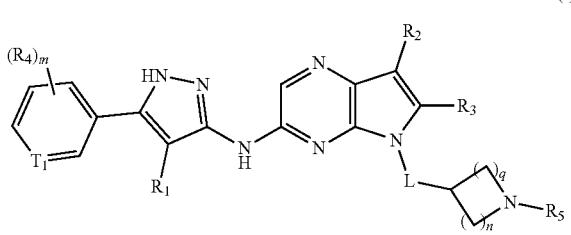

13 Claims, No Drawings
Specification includes a Sequence Listing.

DIAZAINDOLE DERIVATIVE AND USE THEREOF AS CHK1 INHIBITOR

REFERENCE TO SEQUENCE LISTING

The Sequence Listing is submitted concurrently with the specification as an ASCII formatted text file via EFS-Web, with a file name of "P22412942US-2-SEQ", a creation date of Jul. 14, 2022, and a size of 623 bytes. The Sequence Listing filed via EFS-Web is part of the specification and is incorporated in its entirety by reference herein.

The present application is a National Stage of International Application No. PCT/CN2020/132306, filed on Nov. 27, 2020, which claims priorities of the Chinese Patents Application No. CN201911206315.0 filed on Nov. 29, 2019 and Application No. CN202010790385.1 filed on Aug. 7, 2020, the contents of which are incorporated herein by reference in their entireties.

TECHNICAL HELD

The present disclosure relates to a series of diazaindole derivatives and use thereof in the manufacture of a medicament for Chk1-related diseases. The present disclosure specifically relates to a compound represented by formula (I) and a pharmaceutically acceptable salt thereof.

BACKGROUND

Deoxyribonucleic acid (DNA) is the genetic material of the body, and the relative stability of its molecular structure is of great significance to the survival and function of cells. DNA in cells often suffers from various damages because of the interference of various endogenous (such as reactive oxygen species, free radicals and other active compounds generated during metabolism in the body, replication stress response, etc.) and exogenous factors (such as ionizing radiation, ultraviolet rays, alkylating agents, carcinogens, virus infection, etc.). These damages will result in varying degrees of changes in genome that may evolve into transcriptional and replication errors that, if not repaired or incorrectly repaired, ultimately lead to cell death or genetic mutation. There are two most common types of DNA damage: (1) DNA double-strand break (DSB), which is considered to be the most serious DNA damage and is repaired by two different pathways, namely non-homologous end joining (NHEJ) and homologous recombination (HR); (2) DNA single strand break (SSB), a specific type of lesion that occurs at stalled replication forks, but is also a common intermediate formed during DSB repair.

During cell division, its genetic material is duplicated and distributed equally to two daughter cells, going through a series of cell cycles. DNA replication needs to be completed before cells enter the mitotic period (M phase), and damaged DNA must be repaired, otherwise it will trigger a mitotic disaster and cause cell death. To maintain genome integrity, cells have developed a complex mechanism called the DNA damage response (DDR) that mediates the detection and repair of damaged DNA throughout evolution. Simply speaking, cell cycle checkpoints are activated when cellular DNA is damaged, resulting in cell cycle stall, which facilitates DNA repair.

Cell cycle checkpoints have a set of conserved signaling regulatory systems. ATR/Chk1 kinase pathway and ATM/Chk2 kinase pathway play an important role in the molecular mechanism of cell cycle checkpoints involved in DNA damage response. The ATM/Chk2 pathway is usually activated during DNA double-strand breaks, while the ATR/Chk1 pathway is activated during structural damage such as DNA single-strand breaks or DNA alkylation. After the two are activated, a series of downstream substrates, such as Cdc25, cyclin and Wee1, are activated, resulting in cell cycle stall. In the process of signal transmission, the ATR-Chk1-Cdc25 response pathway is the most important pathway for cells to respond to ionizing radiation and replication stress. The principle is roughly that ATR is activated after DNA damage signals are recognized, thereby multiple serine sites on Chk1 are phosphorylated in cells. Activated Chk1 then phosphorylates Cdc25 to accelerate the ubiquitination and degradation of Cdc25; at the same time, activated Chk1 activates Wee1, which in turn phosphorylates and inactivates the CDK1/Cyclin B complex, resulting in cell cycle stall in S and G2/M phases, thereby preventing cells from entering mitosis in the presence of DNA damage or unreplicated DNA.

Some studies have found that Chk1 is highly expressed in some malignant tumors, and tumor cells lacking Chk1 expression tend to show multiple defects, such as slow cell proliferation, disappearance of stagnation response at cell cycle checkpoint, and increased sensitivity to DNA damaging agents. By releasing the blocking effect of Chk1 on cell cycle checkpoints, it promotes tumor cell apoptosis. This mechanism is the research basis of many Chk1 inhibitors and is also a new hot spot in current anti-tumor research. Since nearly 50% of tumor cells are deficient in the tumor suppressor gene p53 resulting in the deletion of G1 checkpoint thereof, most tumor cells mainly rely on the S and G2/M checkpoints, and Chk1 is the main kinase controlling the S and G2/M checkpoints. Therefore, inhibition of Chk1 can hinder the self-repair of tumor cells during DNA damage of tumor cells, thereby achieving the purpose of enhancing the killing of tumor cells. However, normal cells have perfect cell cycle checkpoint regulation functions and can carry out self-repair and protection, so they are relatively insensitive to Chk1 inhibitors, which makes Chk1 inhibitors have good selectivity for targeting tumor cells in tumor therapy.

Chk1 inhibitors can not only be used alone to stop or delay the proliferation of tumor cells, but also can be combined with chemotherapy or radiotherapy to kill tumor cells through a syntheticlethal mechanism to treat tumors. There are various $Chk_1$ inhibitors described in WO 05/066163, WO 04/063198, WO 03/093297, WO 02/070494 and WO 05/009435. LY2606368 (Prexasertib) developed by Lilly Company is undergoing a variety of anti-tumor clinical studies.

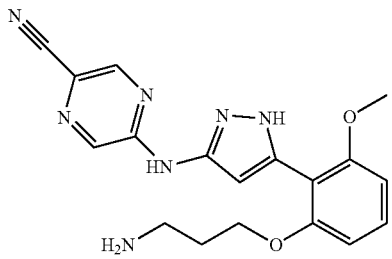

LY2606368

Currently, there is still a need to develop new Chk1 inhibitors for the treatment of cell proliferation-related diseases.

CONTENT OF THE PRESENT INVENTION

The present disclosure provides a compound represented by formula (I) or a pharmaceutically acceptable salt thereof,

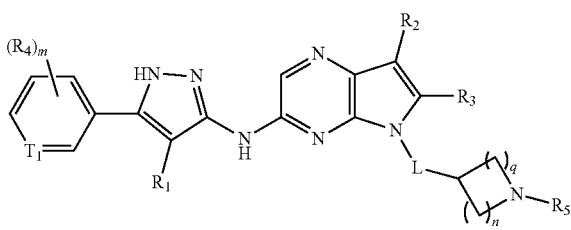

(I)

wherein,
$T_1$ is selected from CH and N;
L is selected from a single bond and —$CH_2$—;
m is selected from 0, 1, 2, 3 and 4;
each of n and q is independently selected from 1 and 2;
$R_1$ is selected from H, F, Cl, Br and I;
$R_2$ is selected from H, D, F, Cl, Br and I;
$R_3$ is selected from H, F, Cl, Br, I, CN and $C_{1-3}$ alkyl, and the $C_{1-3}$ alkyl is optionally substituted by 1, 2 or 3 $R_a$;
each of $R_4$ is independently selected from H, F, Cl, Br, I, $C_{1-3}$ alkyl and $C_{1-3}$ alkoxy, and the $C_{1-3}$ alkyl and $C_{1-3}$ alkoxy are optionally substituted by 1, 2 or 3 $R_b$;
$R_5$ is selected from H and $C_{1-3}$ alkyl, and the $C_{1-3}$ alkyl is optionally substituted by 1, 2 or 3 $R_c$;
each of $R_a$, $R_b$ and $R_c$ is independently selected from H, D, F, Cl, Br and I.

The present disclosure provides a compound represented by formula (I) or a pharmaceutically acceptable salt thereof,

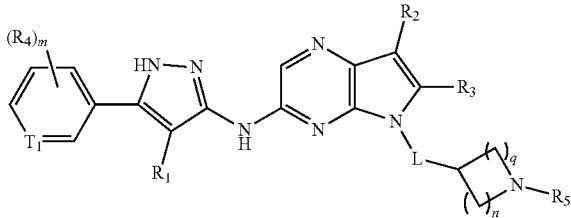

(I)

wherein,
$T_1$ is selected from CH and N;
L is selected from a single bond and —$CH_2$—;
m is selected from 0, 1, 2, 3 and 4;
each of n and q is independently selected from 1 and 2;
$R_1$ is selected from H, F, Cl, Br, I;
$R_2$ is selected from H, D, F, Cl, Br and I;
$R_3$ is selected from H, F, Cl, Br, I, CN and $C_{1-3}$ alkyl, and the $C_{1-3}$ alkyl is optionally substituted by 1, 2 or 3 $R_a$;
each of $R_4$ is independently selected from H, F, Cl, Br, I, $C_{1-3}$ alkyl and $C_{1-3}$ alkoxy, and the $C_{1-3}$ alkyl and $C_{1-3}$ alkoxy are optionally substituted by 1, 2 or 3 $R_b$;
$R_5$ is selected from H and $C_{1-3}$ alkyl, and the $C_{1-3}$ alkyl is optionally substituted by 1, 2 or 3 $R_c$;
each of $R_a$, $R_b$ and $R_c$ is each independently selected from H, F, Cl, Br and I.

In some embodiments of the present disclosure, the $R_1$ is selected from H and F, and other variables are as defined in the present disclosure.

In some embodiments of the present disclosure, the $R_3$ is selected from H and $CH_3$, and other variables are as defined in the present disclosure.

In some embodiments of the present disclosure, each of the $R_4$ is independently selected from H, F, Cl, $CH_3$ and $OCH_3$, and the $CH_3$ and OCH; are optionally substituted by 1, 2 or 3 $R_b$, and other variables are as defined in the present disclosure.

In some embodiments of the present disclosure, each of the $R_4$ is independently selected from H, F, Cl, $CH_3$, $CF_3$, $OCH_3$, $OCD_3$ and $OCF_3$, and other variables are as defined in the present disclosure.

In some embodiments of the present disclosure, each of the $R_4$ is independently selected from H, F, Cl, $CH_3$, $CF_3$, $OCH_3$ and $OCF_3$, and other variables are as defined in the present disclosure.

In some embodiments of the present disclosure, the structural moiety

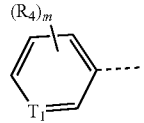

is selected from

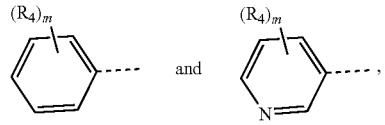

and other variables are as defined in the present disclosure.

In some embodiments of the present disclosure, the structural moiety

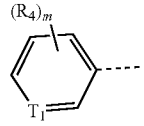

is selected from

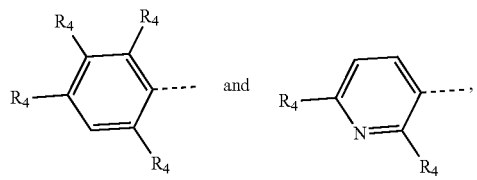

and other variables are as defined in the present disclosure.

In some embodiments of the present disclosure, the structural moiety

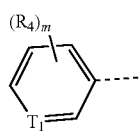

is selected from

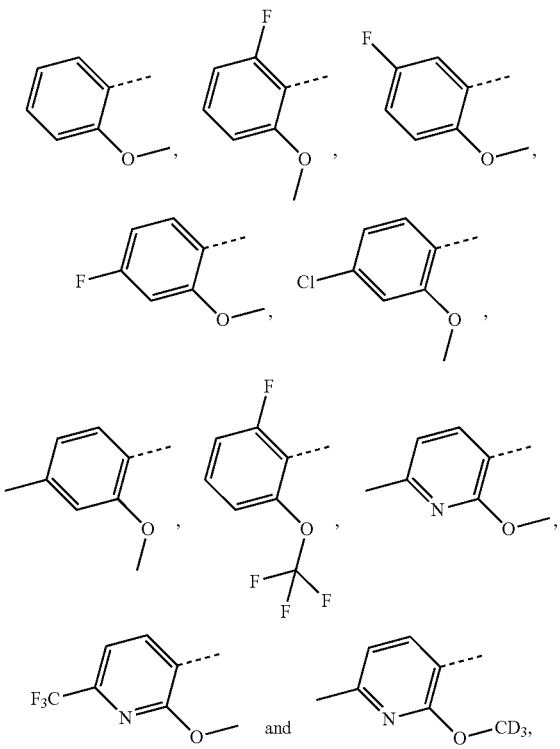

and other variables are as defined in the present disclosure.

In some embodiments of the present disclosure, the structural moiety

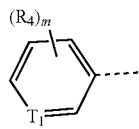

is selected from

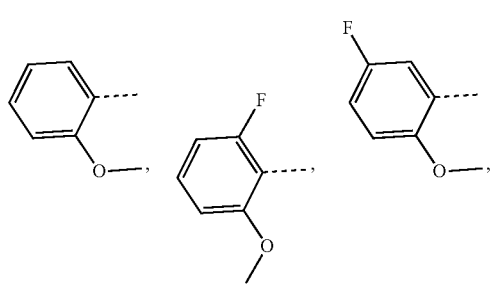

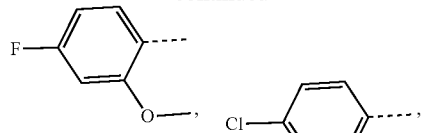

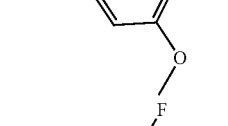

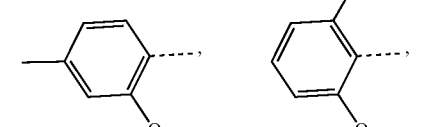

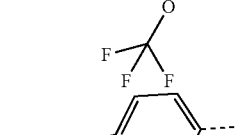

and 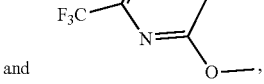

and other variables are as defined in the present disclosure.

In some embodiments of the present disclosure, the $R_5$ is selected from H, $CH_3$ and $CD_3$, and other variables are as defined in the present disclosure.

In some embodiments of the present disclosure, the $R_5$ is selected from H and $CH_3$, and other variables are as defined in the present disclosure.

In some embodiments of the present disclosure, the structural moiety

is selected from

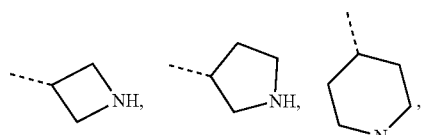

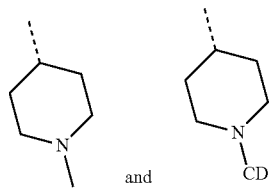

and other variables are as defined in the present disclosure.

In some embodiments of the present disclosure, the structural moiety

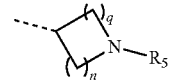

is selected from

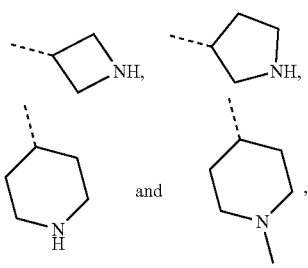

and other variables are as defined in the present disclosure.

In some embodiments of the present disclosure, the structural moiety

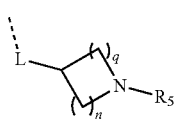

is selected from

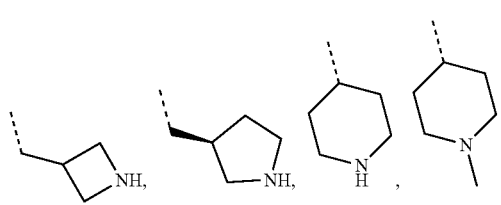

and other variables are as defined in the present disclosure.

In some embodiments of the present disclosure, the structural moiety

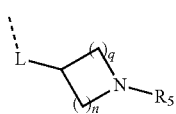

is selected from

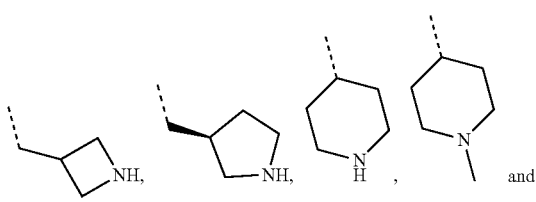

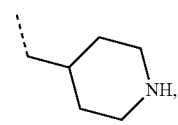

and other variables are as defined in the present disclosure.

In some embodiments of the present disclosure, the compound or the pharmaceutically acceptable salt thereof is selected from

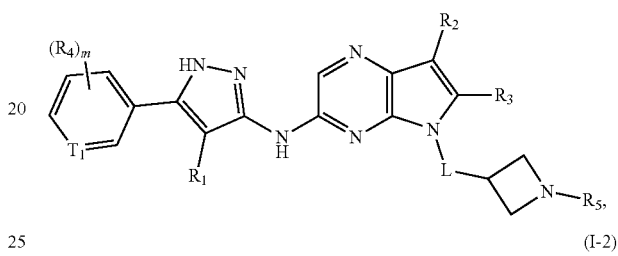

wherein, $T_1$, $R_1$, $R_2$, $R_3$, $R_4$, $R_5$, L and m are as defined in the present disclosure.

There are also some embodiments of the present disclosure that come from any combination of the above variables.

The present disclosure also provides a compound represented by the following formula or a pharmaceutically acceptable salt thereof, wherein the compound is selected from

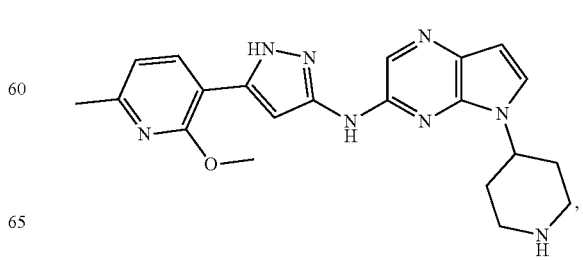

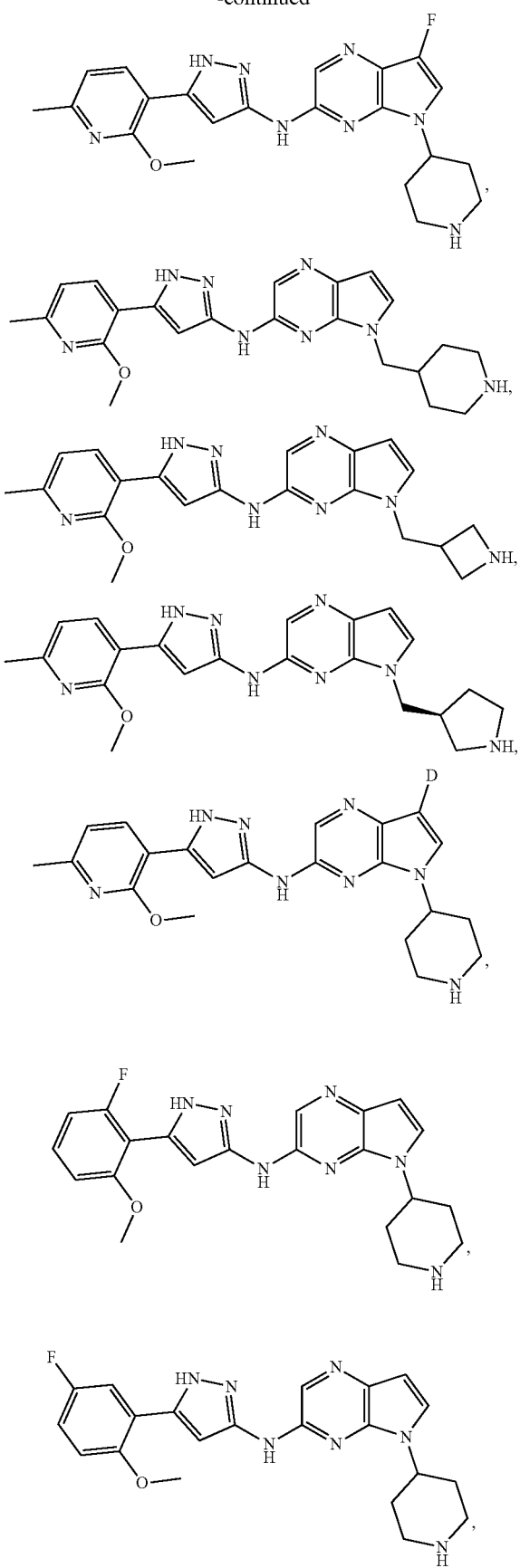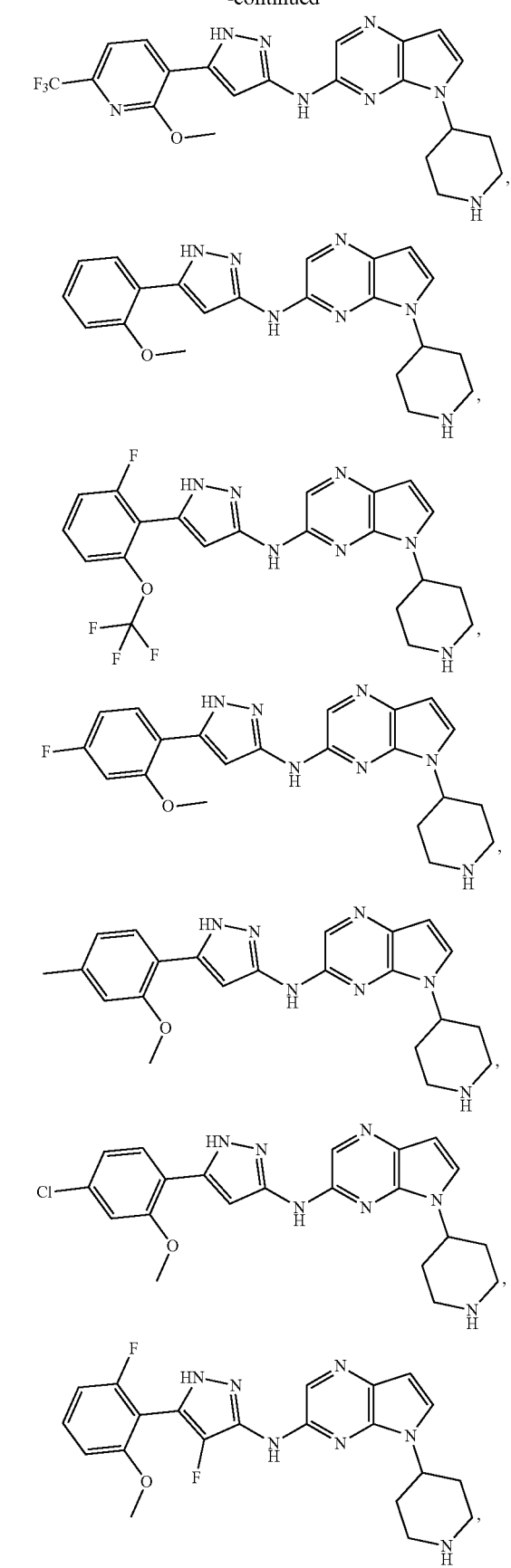

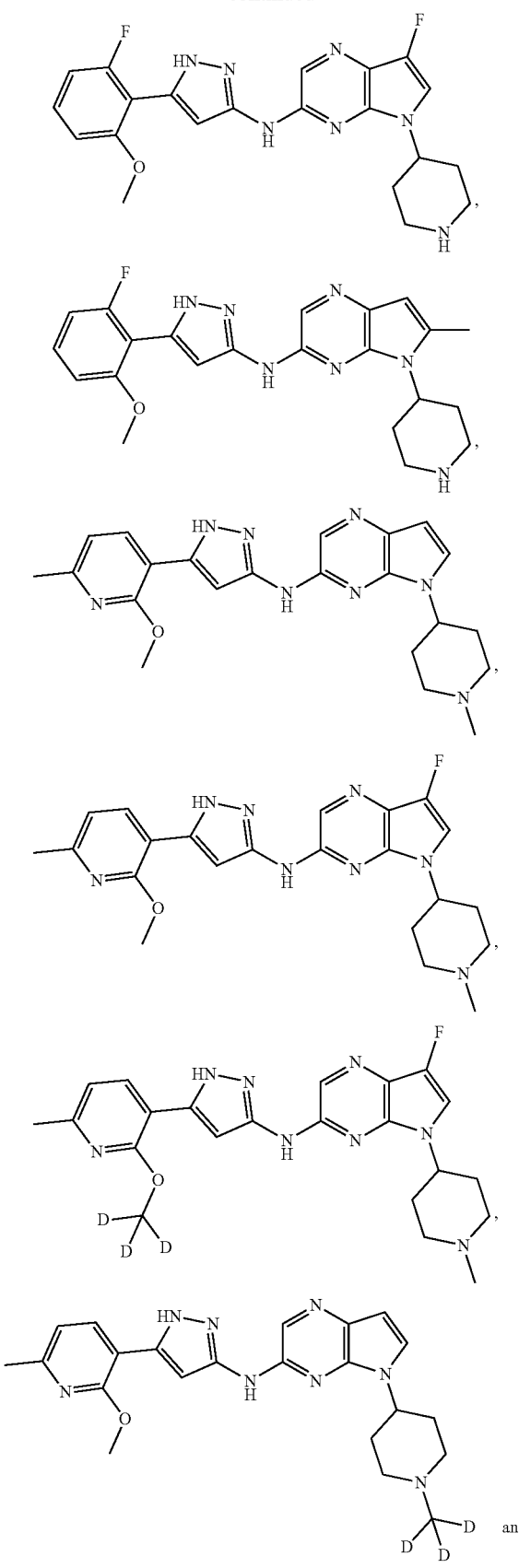

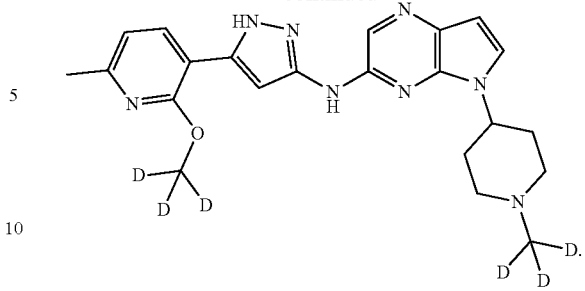

and

The present disclosure also provides use of the compound or the pharmaceutically acceptable salt thereof in the manufacture of a medicament for Chk1-related diseases.

In some embodiments of the present disclosure, the above use is characterized in that, the medicament is a medicament for treating solid tumors such as pancreatic cancer.

Technical Effect

The compounds designed by the present disclosure exhibit good Chk1 inhibitory activity, have good oral exposure and bioavailability, are suitable for oral administration, and representative compounds of the present disclosure used in mouse ovarian cancer models have significant inhibitory effect on inhibiting tumor growth. Therefore, the compounds of the present disclosure have potential application value for the treatment of Chk1-related diseases (such as cell proliferation-related diseases).

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z, is actually A-Z.

Unless otherwise specified, when a group has one or more linkable sites, any one or more sites of the group can be linked to other groups through chemical bonds. When the linking method of the chemical bond is not located, and there are H atoms at the linkable site, when the chemical bond is linked, the number of H atoms at the site will be correspondingly decreased with the number of linked chemical bonds, and the group will be the group with corresponding valence. The chemical bond between the site and other groups can be represented by a straight solid bond (╱ ), a straight dashed bond (╱ ) or a wavy line

For example, the straight solid bond in —OCH$_3$ represents that it is connected to other groups through the oxygen atom in the group; the straight dashed bond in

represents that it is connected to other groups through the two ends of the nitrogen atom in the group; the wavy line in

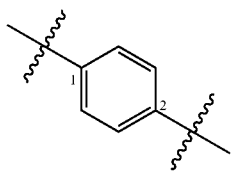 [SMILES: *c1ccc(*)cc1]

represents that the phenyl group is connected to other groups through the 1 and 2 carbon atoms;

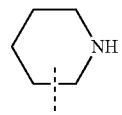

represents that any linkable site on the piperidinyl group can be linked to other groups through 1 chemical bond, and at least includes four linking method of

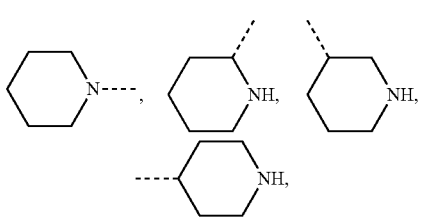

even if there is a H atom on —N—,

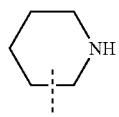

still includes the group with the linking method of

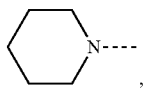

just when the group is linked to a chemical bond, the H at this site will be reduced by 1 correspondingly, and the group will be the corresponding monovalent piperidinyl group.

Unless otherwise specified, the term "D" refers to deuterium ($^3H$).

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, or $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PAM), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with Cukα radiation as the light source and scanning mode: φ/ω scan, and after collecting the relevant data, the crystal structure can be further analyzed by direct method (Shelxs97).

The solvents used in the present disclosure are commercially available. The present disclosure uses the following abbreviations: HCl represents hydrochloric acid; MeOH represents methanol; EtOH represents ethanol; THF represents tetrahydrofuran; DCM represents dichloromethane; DMF represents N,N-dimethylformamide; n-BuLi represents n butyllithium; NaH represents sodium hydride; TFA represents trifluoroacetic acid; min represents minutes.

DETAILED DESCRIPTION OF THE PREFERRED EMBODIMENT

The present disclosure will be described in detail by the following embodiments, but it does not mean any unfavorable limitation of the present disclosure. The present disclosure has been described in detail herein, and specific embodiments thereof have also been disclosed. For those skilled in the art, various changes and modifications made to the specific embodiments of the present disclosure without departing from the spirit and scope of the invention are obvious. The hydrochloride or trifluoroacetate of the compound of the present disclosure was added to sodium bicarbonate solution, and the mixture was extracted with ethyl acetate, and then the organic phase was dried with anhydrous sodium sulfate, and concentrated under reduced pressure to obtain the corresponding compound. Alternatively, the hydrochloride or trifluoroacetate of the compound of the present disclosure was added to a saturated sodium bicarbonate solution, and the pH was adjusted to neutrality, and then the mixture was separated by high performance liquid chromatography (neutral, ammonium bicarbonate system) to obtain the free base of the compound.

Embodiment 1

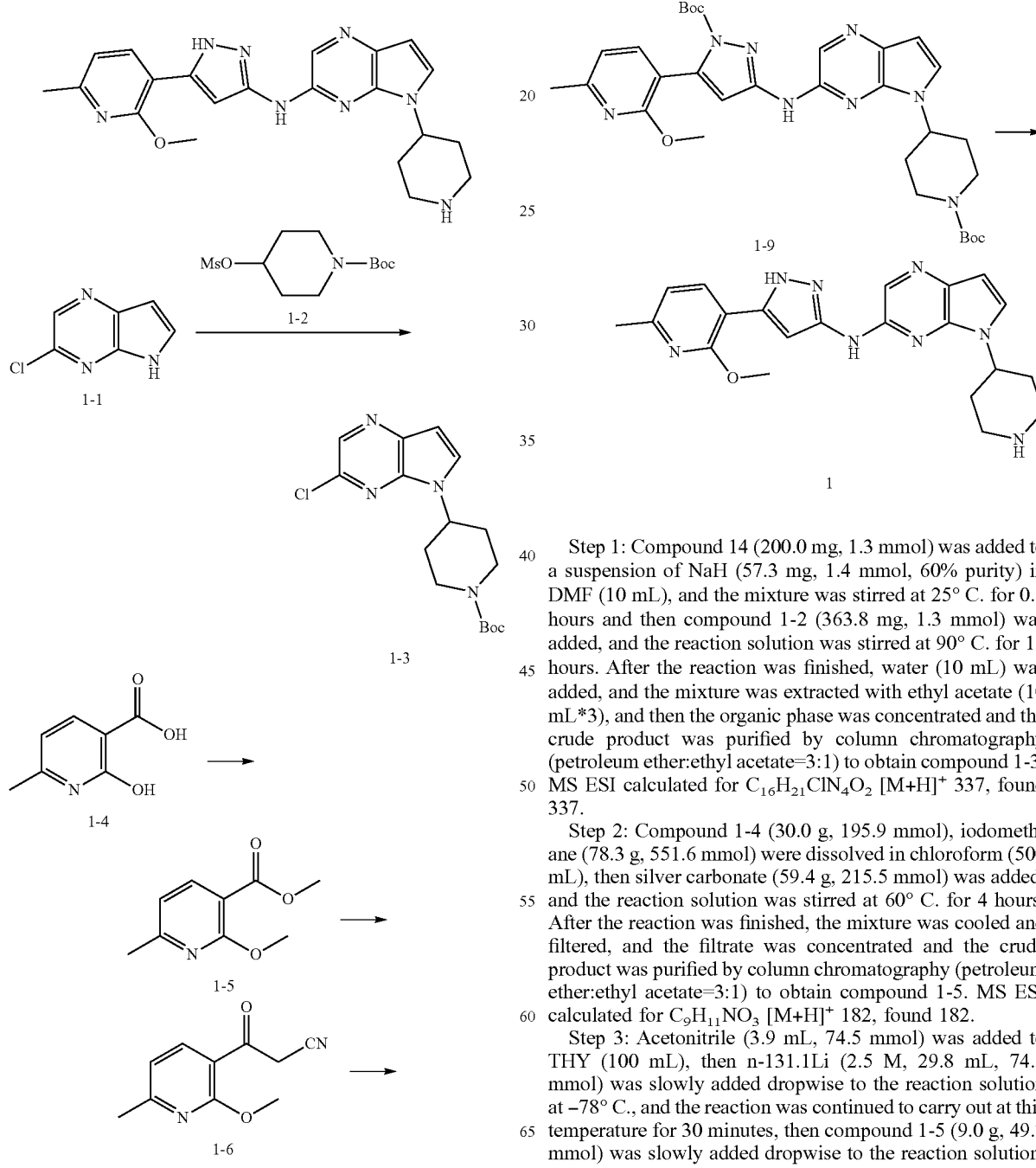

Step 1: Compound 14 (200.0 mg, 1.3 mmol) was added to a suspension of NaH (57.3 mg, 1.4 mmol, 60% purity) in DMF (10 mL), and the mixture was stirred at 25° C. for 0.5 hours and then compound 1-2 (363.8 mg, 1.3 mmol) was added, and the reaction solution was stirred at 90° C. for 16 hours. After the reaction was finished, water (10 mL) was added, and the mixture was extracted with ethyl acetate (10 mL*3), and then the organic phase was concentrated and the crude product was purified by column chromatography (petroleum ether:ethyl acetate=3:1) to obtain compound 1-3. MS ESI calculated for $C_{16}H_{21}ClN_4O_2$ [M+H]$^+$ 337, found 337.

Step 2: Compound 1-4 (30.0 g, 195.9 mmol), iodomethane (78.3 g, 551.6 mmol) were dissolved in chloroform (500 mL), then silver carbonate (59.4 g, 215.5 mmol) was added, and the reaction solution was stirred at 60° C. for 4 hours. After the reaction was finished, the mixture was cooled and filtered, and the filtrate was concentrated and the crude product was purified by column chromatography (petroleum ether:ethyl acetate=3:1) to obtain compound 1-5. MS ESI calculated for $C_9H_{11}NO_3$ [M+H]$^+$ 182, found 182.

Step 3: Acetonitrile (3.9 mL, 74.5 mmol) was added to THY (100 mL), then n-131.1Li (2.5 M, 29.8 mL, 74.5 mmol) was slowly added dropwise to the reaction solution at −78° C., and the reaction was continued to carry out at this temperature for 30 minutes, then compound 1-5 (9.0 g, 49.7 mmol) was slowly added dropwise to the reaction solution, and the reaction was continued to carry out for 30 minutes, and then the reaction solution was heated to room temperature. The reaction solution was poured into water (100 mL), and extracted with ethyl acetate (200 mL). Then the organic phase was concentrated, and the crude product was purified by column chromatography (petroleum ether:ethyl acetate=2:1) to obtain compound 1-6. MS ESI. calculated for $C_{10}H_{10}N_2O_2$ [M+H]$^+$ 191, found 191.

Step 4: Compound 1-6 (8.0 g, 42.1 mmol) was dissolved in ethanol (50 mL), then hydrazine hydrate (12.6 g, 252.4 mmol, 12.27 mL) and acetic acid (8.0 mL, 139.8 mmol) were added successively, and the reaction solution was stirred at 100° C. for 2 hours. After the reaction was finished, the reaction solution was concentrated, and the crude product was purified by column chromatography (petroleum ether:ethyl acetate=1:1) to obtain compound 1-7. MS ESI. calculated for $C_{10}H_{12}N_4O_3$ [M+H]$^+$ 205. found 205.

Step 5: Compound 1-7 (9.5 g, 46.5 mmol) was dissolved in THF (50 mL), then NaH (2.1 g, 51.2 mmol, 60% purity) was added at 0° C. and the reaction solution was stirred for 0.5 hours, then di-tert-butyl dicarbonate (11.2 g, 51.2 mmol) was added; the reaction was carried out at 0° C. for 0.5 hours, and then the reaction solution was concentrated, and the crude product was purified by column chromatography (petroleum ether:ethyl acetate=1:1) to obtain compound 1-8. MS ESI calculated for $C_{15}H_{20}N_4O_3$ [M+H]$^+$ 305, found 305.

Step 6: Compound 1-3 (130.0 mg, 0.4 mmol) and compound 1-8 (117.4 mg, 0.4 mmol) were dissolved in 1,4-dioxane (10 mL), and then cesium carbonate (188.6 mg, 0.6 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladitum(II) (35.0 mg, 0.4 mmol) were added successively, and the reaction solution was stirred at 95° C. for 3 hours; after filtration, the filtrate was concentrated to obtain compound 1-9. MS ESI calculated for $C_{31}H_{40}N_8O_5$ [M+H]$^+$ 605, found 605.

Step 7: Compound 1-9 (0.1 g, 0.16 mmol) was dissolved in dichloromethane (3 mL), then trifluoroacetic acid (3 mL) was added, and the reaction solution was stirred at 25° C. for 0.5 hours. After the reaction was finished, the reaction solution was concentrated, and the crude product was separated by preparative high performance liquid chromatography (chromatographic column: Boston Prime C18 150*30 mm 5 μm; mobile phase: [water (0.05% ammonia water)-acetonitrile]; acetonitrile %: 36%-46%, 9 min) to obtain compound 1. $^1$H NMR (400 MHz, CD$_3$OD) δ 8.21 (s, 1H), 7.97 (d, J=7.53 Hz, 1H), 7.49 (d, J=3.76 Hz, 1H), 7.03-7.05 (brs, 1H), 6.95 (d, J=7.53 Hz, 1H), 6.52 (d, J=4.02 Hz, 1H), 4.69-4.81 (m, 1H), 4.11 (s, 3H), 3.26 (br d, J=14.05 Hz, 2H), 2.86 (dr t, J=11.92 Hz, 2H), 2.50 (s, 3H), 1.95-2.18 (m, 4H). MS ESI calculated for $C_{21}H_{24}N_8O$ [M+H]$^+$ 405, found 405.

Embodiment 2

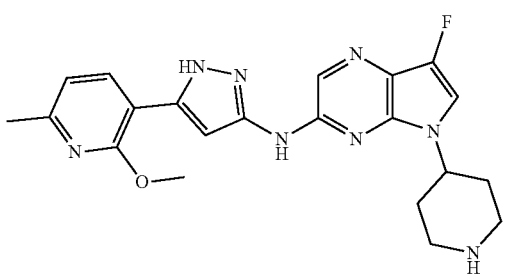

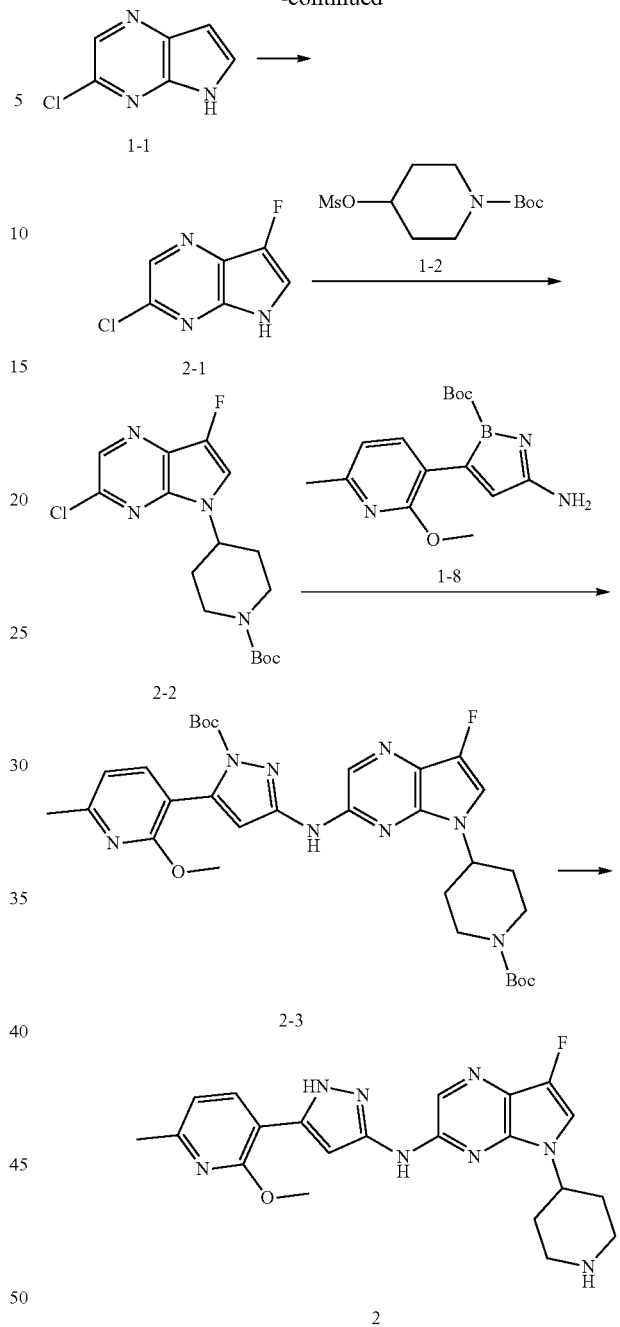

Step 1: Compound 1-1 (0.2 g, 1.3 mmol) was dissolved in acetonitrile (5 mL), then 1-chloromethyl-4-fluoro-1,4-diazabicyclo[2.2.2]octane bis(tetrafluoroborate) (551.7 mg, 1.6 mmol) and pyridine (754.4 mg, 9.5 mmol) were added successively; the reaction solution was stirred at 25° C. for 12 hours, then the reaction solution was concentrated, and the crude product was purified by column chromatography (petroleum ether:ethyl acetate=1:1) to obtain compound 2-1. MS ESI calculated for $C_6H_3ClFN_3$ [M+H]$^+$ 172, found 172.

Step 2: Compound 2-1 (100.0 mg, 582.9 μmol) was dissolved in DMF (5 mL), then NaH (34.9 mg, 874.3 μmol, 60% purity) was added at 25° C., and the mixture was stirred for 1 hour, then 1-2 (162.8 mg, 582.9 μmol) was added, and the reaction solution was stirred at 80° C. for 2 hours; water (10 mL) and ethyl acetate (50 mL) were added for extraction, and then the organic phase was concentrated. The crude product was purified by column chromatography (petroleum ether:ethyl acetate=3: 1) to obtain the compound 2-2. MS ESI calculated for $C_{16}H_{20}ClFN_4O_2$ [M+H]$^+$ 355, found 355.

Step 3: Compound 2-2 (60.0 mg, 169.1 μmol) and 1-8 (40.0 mg, 131.4 μmol) were dissolved in 1,4-dioxane (5 mL), then methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) and cesium carbonate (85.6 mg, 262.8 μmol) were added successively, and the reaction solution was stirred under nitrogen protection at 90° C. for 2 hours, after the reaction was finished, the reaction solution was cooled and filtered, and the filtrate was concentrated to obtain a crude product of compound 2-3, which was directly used in the next reaction. MS ESI calculated for $C_{31}H_{39}FN_8O_5$ [M+H]$^+$ 623, found 623.

Step 4: Compound 2-3 (30.5 mg, 48.5 μmol) was dissolved in dichloromethane (2 mL), then trifluoroacetic acid (2 mL) was added, and the reaction solution was stirred at 25° C. for 0.5 hours. After the reaction was finished, the reaction solution was concentrated, and the crude product was separated by preparative high performance liquid chromatography (chromatographic column: Xtimate C18 150*25 mm*5 μm; mobile phase: [water (0.075% TFA)-acetonitrile]; acetonitrile %: 24%-44%, 7 min) to obtain the trifluoroacetate of compound 2. $^1$H NMR (400 MHz, CD$_3$OD) δ 8.25 (s, 1H), 8.00 (d, J=7.53 Hz, 1H), 7.36-7.39 (m, 1H), 6.96 (d, J=7.53 Hz, 1H), 6.84 (s, 1H), 5.14 (br s, 1H), 4.94-5.03 (m, 2H), 4.79-4.87 (m, 1H), 4.10 (s, 3H), 3.62 (br d, J=12.80 Hz, 2H), 3.36-3.39 (m, 2H), 2.50 (s, 3H), 2.18-2.43 (m, 4H). MS ESI calculated for $C_{21}H_{23}FN_8O$ [M+H]$^+$ 423, found 423.

Embodiment 3

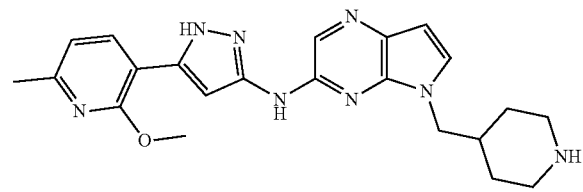

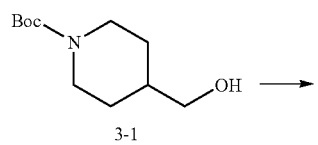

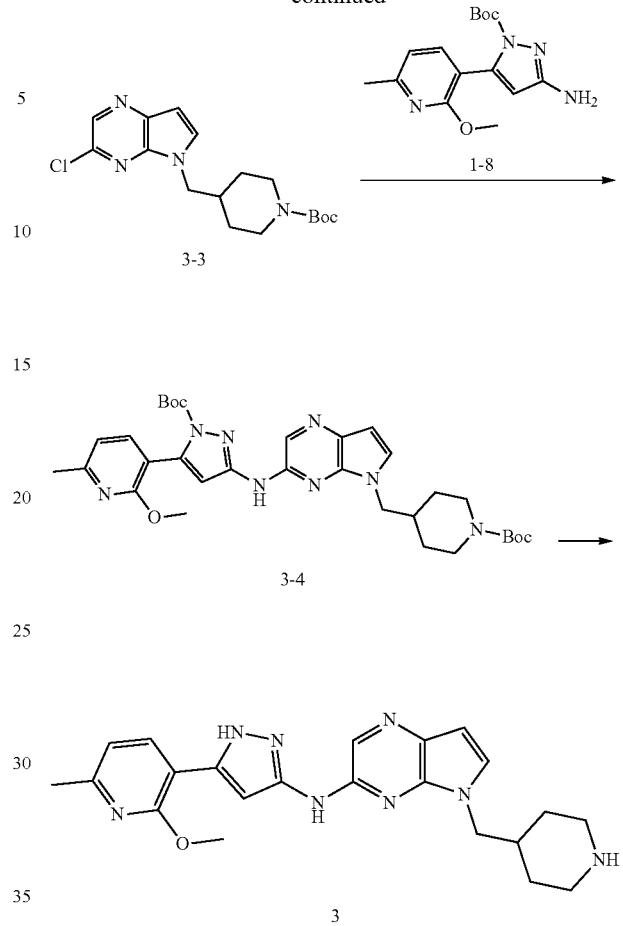

Step 1: Compound 3-1 (0.5 g, 2.3 mmol) and triethylamine (352.5 mg, 3.5 mmol) were dissolved in dichloromethane (30 mL), then methanesulfonyl chloride (399.1 mg, 3.5 mmol) was added to the reaction solution and the reaction was carried out at 25° C. for 0.5 hours. After the reaction was finished, the reaction solution was concentrated, and the crude product was purified by column chromatography (petroleum ether:ethyl acetate=5:1) to obtain compound 3-2. MS ESI calculated for $C_{12}H_{23}NO_5S$ [M+H]$^+$ 294, found 294.

Step 2: Compound 1-1 (156.6 mg, 1.0 mmol) was dissolved in DMF (10 mL), then NaH (61.20 mg, 1.53 mmol, 60% purity) was added, and the mixture was stirred at 25° C. for 1 hour, and then 3-2 (0.3 g, 1.0 mmol) was added, and the reaction was continued to carry out at 90° C. for 2 hours; then water (10 mL) was added, and the mixture was extracted with ethyl acetate, concentrated, and the crude product was purified by column chromatography (petroleum ether:ethyl acetate=3:1) to obtain compound 3-3. MS ESI calculated for $C_{17}H_{23}ClN_4O_2$[M+H]$^+$ 351, found 351.

Step 3: Compound 3-3 (115.3 mg, 328.6 μmol) and 1-8 (100.0 mg, 328.6 μmol) were dissolved in 1,4-dioxane (5 mL), then methanesulfonato(2-dicyclohexylphosphino-3,6-dimethoxy-2'-4'-6'-tri-i-propyl-1,1'-bipheny(2'-amino-1,1'-biphenyl-2-yl)palladium(II) (29.8 mg, 32.9 μmol) and cesium carbonate (214.1 mg, 657.2 μmol) were added to the reaction solution, respectively, and the reaction was carried out at 90° C. for 0.5 hours under nitrogen protection. After the reaction was finished, the reaction solution was concentrated to obtain a crude product of compound 3-4, which was directly used in the next reaction. MS ESI calculated for $C_{32}H_{42}NO_5$ [M+H]$^+$ 619, found 619.

Step 4: Compound 3-4 (150.2 mg, 242.8 μmol) was dissolved in dichloromethane (2 mL), then trifluoroacetic acid (2 mL) was added, and the mixture was stirred at 25° C. for 0.5 hours. After the reaction was finished, the reaction solution was concentrated. The crude product was separated by preparative high performance liquid chromatography (chromatographic column: Xtimate C18 150*25 mm*5 μm; mobile phase: [water (0.075% TFA)-acetonitrile]; acetonitrile %: 15%-45%, 7 ma) to obtain the trifluoroacetate of compound 3. $^1$H NMR (400 MHz, CD$_3$OD) δ 8.25 (s, 1H), 7.99 (d, J=7.78 Hz, 1H), 7.56 (d, J=3.76 Hz, 1H), 6.95 (d, J=7.78 Hz, 1H), 6.81 (s, 1H), 6.60 (d, J=3.76 Hz, 1H), 4.71-4.96 (d, 1H), 4.42 (d, J=7.03 Hz, 2H), 4.11 (s, 3H), 3.34-3.41 (m, 2H), 2.93 (dt, J=2.76, 12.92 Hz, 2H), 2.48 (s, 3H), 2.14-2.40 (m, 1H), 1.96 (s, 1H), 1.83 (br d, J=12.55 Hz, 2H), 1.41-1.63 (m, 2H). MS ESI calculated for $C_{22}H_{26}N_8O$ [M+H]$^+$ 419, found 419.

The compounds shown in Table 1 were prepared with reference to the method of compound 3 using the corresponding alcohols as starting materials:

TABLE 1

| Embodiment | Starting material | Structural formula | Separation method, $^1$HNMR & LCMS |
|---|---|---|---|
| 4 | 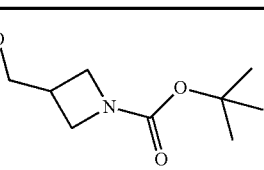 | 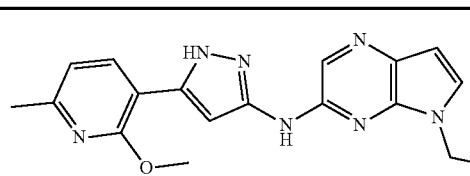
Compound 4 | Chromatographic column: Boston Green ODS 150*30 mm 5 μm; mobile phase: [water (0.075% TFA)-acetonitrile]; acetonitrile %: 22%-42%, 7 min. Trifluoroacetate of compound 4, $^1$H NMR (400 MHz, CD$_3$OD) δ 8.20 (s, 1H), 7.99 (d, J = 7.78 Hz, 1H), 7.56 (d, J = 3.76 Hz, 1H), 6.91-6.97 (brs 1 H), 6.90 (d, J = 7.78 Hz, 1H), 6.60 (d, J = 3.76 Hz, 1H), 4.69-4.71 (m, 2H), 4.01-4.05 (m, 7H), 3.49-3.56 (m, 1H), 2.45 (s, 3H). MS ESI calculated for $C_{20}H_{22}N_8O$ [M + H]$^+$ 391, found 391. |

TABLE 1-continued

| Embodiment | Starting material | Structural formula | Separation method, ¹HNMR & LCMS |
|---|---|---|---|
| 5 | | 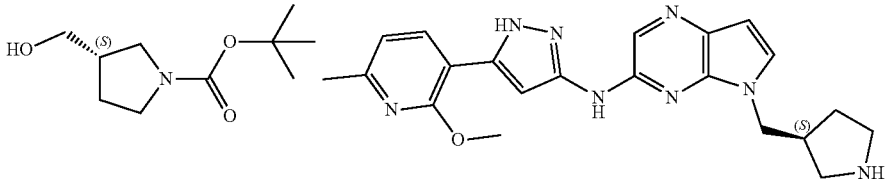Compound 5 | Chromatographic column: Boston Green ODS 150*30 mm 5 μm; mobile phase: [water (0.075% TFA)-acetonitrile]; acetonitrile %: 22%-42%, 7 min. Trifluoroacetate of compound 5, ¹H NMR (400 MHz, CD₃OD) δ 8.20 (s, 1H), 7.99 (d, J = 7.78 Hz, 1H), 7.56 (d, J = 3.76 Hz, 1H), 6.91-6.97 (brs 1 H), 6.90 (d, J = 7.78 Hz, 1H), 6.58 (d, J = 3.76 Hz, 1H), 4.51-4.61 (m, 2H), 4.07 (s, 3 H), 3.35-3.46 (m, 2H), 3.32-3.26 (m, 1H), 3.12-3.16 (m, 1H), 2.95-3.09 (m, 1H), 2.45 (s, 3H), 2.22-2.26 (m, 1H), 1.80-1.86 (m, 1H). MS ESI calculated for C₂₁H₂₄N₈O [M + H]⁺ 405, found 405. |

Embodiment 6

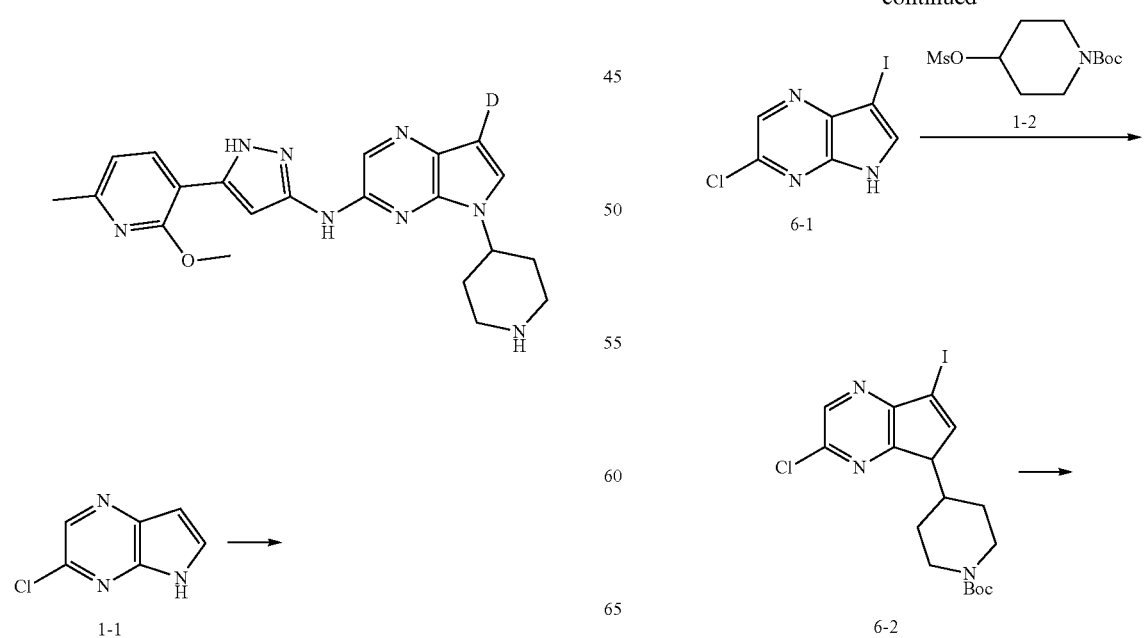

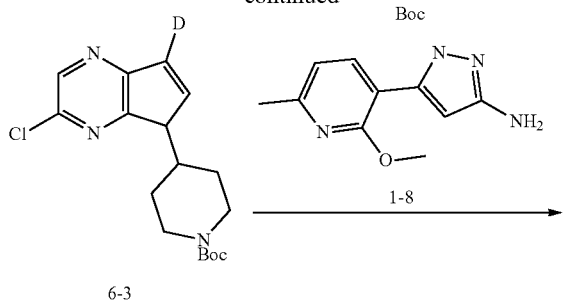

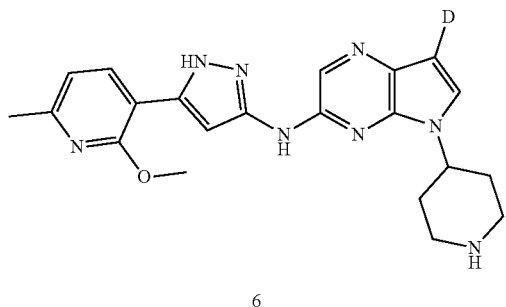

raphy (petroleum ether:ethyl acetate=2:1) to obtain compound 6-2. MS ESI calculated for $C_{16}H_{20}ClN_4O_2[M+H]^+$ 463, found 463.

Step 3: Compound 6-2 (0.9 g, 1.9 mmol) was dissolved in THF (10 mL), then n-BuLi (2.5 M, 394.20 μL) was added dropwise at −78° C. under nitrogen protection, and the mixture was stirred at −78° C. for 0.5 hours, then deuterium water (32.9 mg, 1.6 mmol) was added and the reaction solution was stirred for half an hour; after the reaction was finished, saturated brine (2 mL) was added to quench the reaction, and the mixture was extracted with ethyl acetate (50 mL), and then the organic phase was dried and concentrated to obtain compound 6-3, which was directly used in the next reaction. MS ESI calculated for $C_{16}H_{20}DClN_4O_2$ $[M+H]^+$ 338, found 338.

Step 4: Compound 6-3 (270.0 mg, 799.24 μmol) and compound 1-8 (342.0 mg, 1.9 mmol) were dissolved in 1,4-dioxane (10 mL), then methanesulfonato(2-dicyclohexylphosphino-3,6-dimethoxy-2'-4'-6'-tri-i-propyl-1,1'-biphenyl)(2'-amino-1,1'-biphenyl-2-yl)palladium(II) and cesium carbonate (520.8 mg, 1.6 mmol) were added successively, and the reaction solution was stirred at 100° C. for 1.5 hours. After the reaction was finished, the reaction solution was cooled and filtered, and the filtrate was concentrated to obtain compound 6-4, which was directly used in the next reaction. MS ESI calculated for $C_{31}H_{39}DN_8O_5$ $[M+H]^+$ 606, found 606.

Step 5: Compound 6-4 (0.1 g, 0.2 mmol) was dissolved in dichloromethane (3 mL), then trifluoroacetic acid (3 mL) was added, and the mixture was stirred at 25° C. for 0.5 hours. After the reaction was finished, the reaction solution was concentrated. The crude product was separated by preparative high performance liquid chromatography (chromatographic column: Waters Xbridge 150*25 5μ, mobile phase: [water (10 mM $NH_4HCO_3$)-acetonitrile]; acetonitrile %: 0%-60%, 10 min.) to obtain compound 6. $^1H$ NMR (400 MHz, $CD_3OD$) δ 8.21 (s, 1H), 7.96 (d, J=7.5 Hz, 1H), 7.48 (s, 1H), 7.09-6.92 (m, 2H), 4.10 (s, 3H), 3.28 (br d, J=13.1 Hz, 3H), 2.96-2.84 (m, 3H), 2.50 (s, 3H), 2.19-2.02 (m, 4H). MS ESI calculated for $C_{21}H_{23}DN_8O$ $[M+H]^+$ 406, found 406.

Embodiment 7

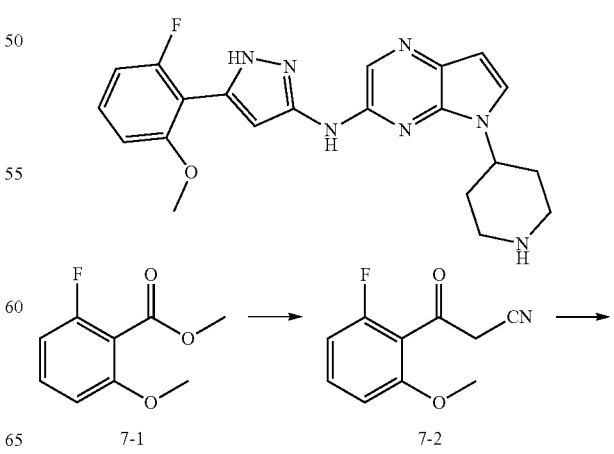

Step 1: Compound 1-1 (1.0 g, 6.5 mmol) was dissolved in DMF (20 mL), then KOH (1.5 g, 26.1 mmol) and iodine granules (3.3 g, 13.0 mmol) were added at 0° C., and the reaction solution was stirred at 0° C. for 1 hour, then heated to 25° C. and continued to stir for 2 hours. After the reaction was finished, ice water (100 mL) was added and the mixture was filtered, and the filter cake was dried to obtain a crude product of compound 6-1, which was directly used in the next reaction. MS ESI calculated for $C_6H_3ClIN_3$ $[M+H]^+$ 280, found 280.

Step 2: Compound 6-1 (1.6 g, 5.7 mmol) was dissolved in DMF (50 mL), then NaH (343.5 mg, 8.6 mmol, 60% purity) was added at 0° C., and the temperature was naturally raised to 25° C. and the reaction solution was stirred for half an hour. Then compound 1-2 (4.8 g, 17.2 mmol) was added and the reaction solution was heated to 80° C. and stirred for 12 hours. After the reaction was finished, the reaction solution was concentrated. The concentrated solution was diluted with ethyl acetate (80 mL) and washed with water (50 mL) and brine (50 mL) respectively. The organic phase was dried and concentrated, and then purified by column chromatog-

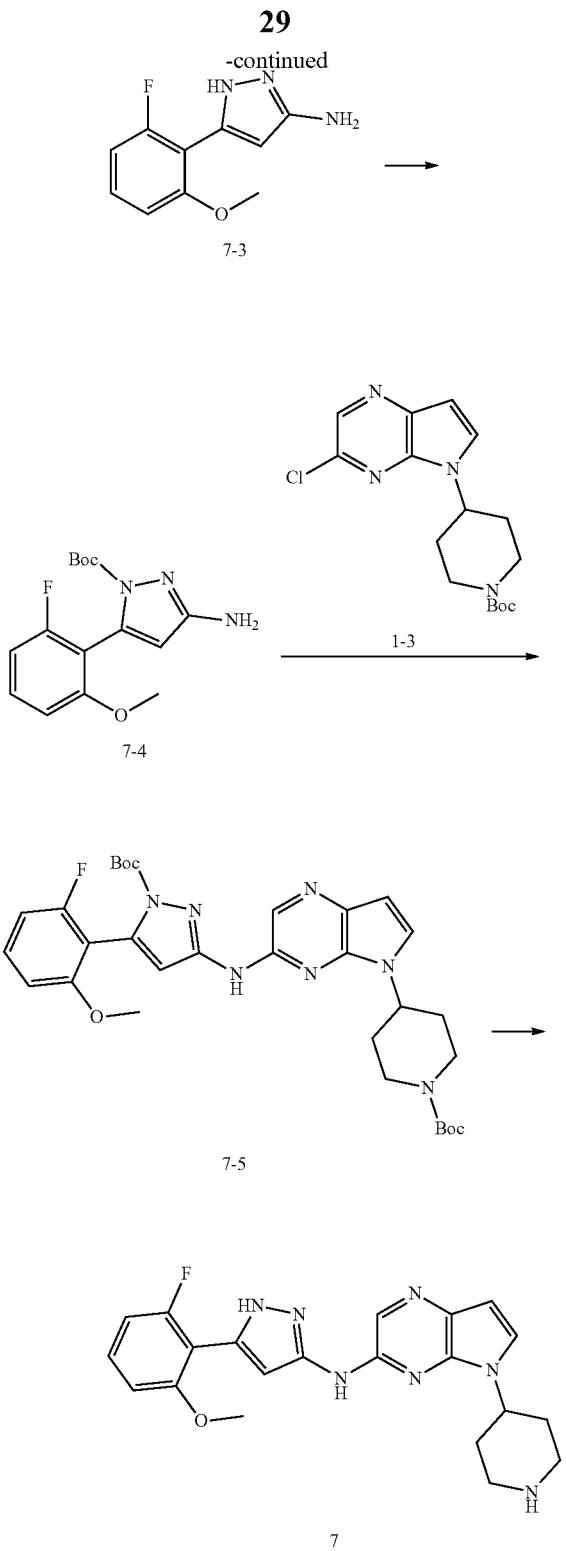

Step 1: n-BuLi (4.3 mL, 2.5 M) was added to a solution of acetonitrile (445.8 mg, 10.8 mmol) in THF (10 mL) at −78° C., and the reaction solution was stirred at −78° C. for 0.5 hours, and then a solution of compound 7-1 (1.0 g, 5.4 mmol) in THF (5 mL) was added dropwise, and the reaction mixture was stirred at −78° C. for 0.5 hours. After the reaction was finished, 10% aqueous citric acid solution (5 mL) was added to quench, and the reaction solution was extracted with ethyl acetate (50 mL), dried and concentrated to obtain a crude product of compound 7-2, which was directly used in the next step. MS ESI calculated for $C_{10}H_8FNO_2$ [M+H]$^+$ 194, found 194.

Step 2: Hydrazine hydrate (0.8 mL, 15.6 mmol) was added dropwise to a solution of compound 7-2 (117.5 mg, 0.4 mmol) in ethanol (10 mL) and acetic acid (1 mL), and the reaction solution was stirred at 100° C. for 2 hours; after the reaction was finished, the reaction solution was concentrated, and the crude product was purified by column chromatography (petroleum ether:ethyl acetate=1:1) to obtain compound 7-3. MS ESI calculated for $C_{10}H_{10}FN_3O$ [M+H]$^+$ 208, found 208.

Step 3: Compound 7-3 (1.0 g, 4.8 mmol) was added to a suspension of NaH (231.6 mg, 5.8 mmol, 60% purity) in THF (10 mL) at 0° C., then the reaction mixture was stirred at 0° C. for 0.5 hours, and then di-tert-butyl carbonate (1.7 g, 5.8 mmol) was added to the reaction and the reaction mixture was stirred at 25° C. for 0.5 hours. After the reaction was finished, water was added, and the mixture was extracted with ethyl acetate, and the crude product after concentration was purified by column chromatography (petroleum ether:ethyl acetate=3:1) to obtain compound 7-4. MS ESI calculated for $C_{15}H_{18}FN_3O_3$[M+H]$^+$ 308, found 308.

Step 4: Compound 7-4 (60.0 mg, 0.2 mmol), compound 1-3 (74.4 mg, 0.2 mmol) were dissolved in 1,4-dioxane (10 mL), and then cesium carbonate (95.4 mg, 0.3 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (17.7 mg, 0.02 mmol) were added successively, then the mixture was stirred at 95° C. for 3 hours, after the reaction was finished, the reaction solution was filtered and concentrated to obtain a crude product of compound 7-5, which was directly used in the next step. MS ESI calculated for $C_{31}H_{38}FN_7O_5$ [M+H]$^+$ 608, found 608.

Step 5: Compound 7-5 (110.0 mg, 0.2 mmol) was dissolved in dichloromethane (2 mL), then trifluoroacetic acid (2 mL) was added, and the mixture was stirred at 25° C. for 0.5 hours. After the reaction was finished, the reaction solution was concentrated and the crude product was separated by preparative high performance liquid chromatography (chromatographic column: Phenomenex Ge min.i-NX 150*30 mm*5 μm; mobile phase. [water (10 mM $NH_4HCO_3$)-acetonitrile]; acetonitrile %: 27%-49.5%, 6 min) to obtain compound 7. $^1$H NMR (400 MHz, CD$_3$OD) δ 8.18 (s, 1H), 7.47 (d, J=3.50 Hz, 1H), 7.35-7.43 (m, 1H), 7.29 (br s, 1H), 7.03 (d, J=8.50 Hz, 1H), 6.87-6.95 (m, 1H), 6.52 (d, J=3.63 Hz, 1H), 4.63 (br s, 1H), 4.02 (s, 3H), 3.27 (br s, 2H), 2.90 (br t, J=11.88 Hz, 2H), 1.98-2.20 (m, 4H). MS ESI calculated for $C_{21}H_{22}FN_7O$ [M+H]$^+$ 408, found 408.

The compounds shown in Table 2 were prepared with reference to the method of compound 7 using the corresponding esters as starting materials:

TABLE 2

| Embodiment | Starting material | Structural formula | Separation method, ¹HNMR & LCMS |
|---|---|---|---|
| 8 | 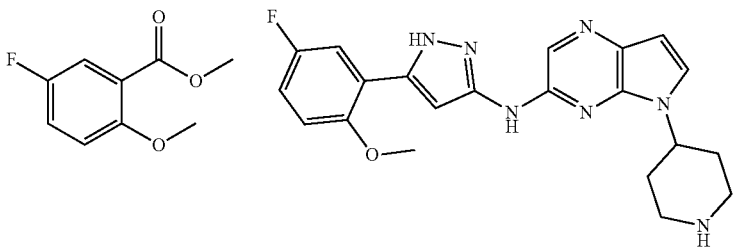 | Compound 8 | Chromatographic column: Boston Green ODS 150*30 mm 5 μm; mobile phase, [water (0.075% TFA)-acetonitrile]; acetonitrile %: 27%-47%, 7 min. Trifluoroacetate of compound 8, $^1$H NMR (400 MHz, CD$_3$OD) δ 8.22 (br s, 1H), 7.49 (br d, J = 3.8 Hz, 2H), 7.19-7.05 (m, 2H), 7.23-7.01 (m, 1H), 6.53 (d, J = 3.5 Hz, 1H), 4.62 (br s, 1H), 3.99 (s, 3H), 3.37 (br s, 1H), 3.39-3.34 (m, 1H), 2.97 (br t, J = 12.2 Hz, 2H), 2.26-2.07 (m, 4H). MS ESI calculated for C$_{21}$H$_{22}$FN$_7$O [M + H]$^+$ 408, found 408. |
| 9 | 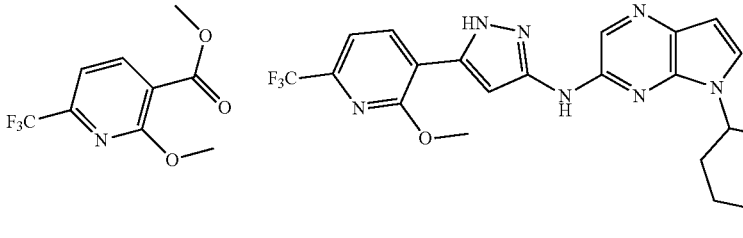 | Compound 9 | Chromatographic column: Boston Green ODS 150*30 mm 5 μm; mobile phase, [water (0.075% TFA)-acetonitrile]; acetonitrile %: 26%-56%, 7 min. Trifluoroacetate of compound 9, $^1$H NMR (400 MHz, CD$_3$OD) δ 8.34 (d, J = 6.8 Hz, 1H), 8.24 (br s, 1H), 7.50 (br d, J = 7.5 Hz, 2H), 6.97 (br s, 1H), 6.59 (d, J = 3.5 Hz, 1H), 5.03 (br s, 1H), 4.60 (br s, 2H), 4.17 (s, 3H), 3.57-3.70 (m, 2H), 2.26-2.48 (m, 4H). MS ESI calculated for C$_{21}$H$_{21}$F$_3$N$_8$O [M + H]$^+$ 459, found 459. |
| 10 | 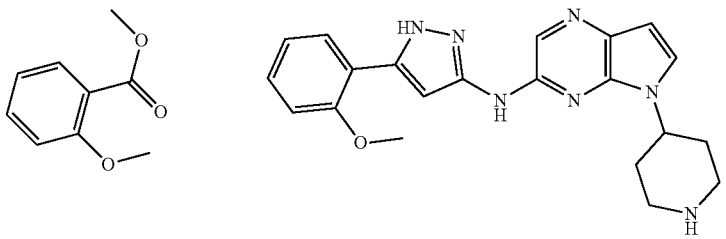 | Compound 10 | Chromatographic column: Venusil ASB Phenyl 250*50 mm 10 μm; mobile phase: [water (0.05% HCl)-acetonitrile]; acetonitrile %: 20%-46%, 9 min. Hydrochloride of compound 10, $^1$H NMR (400 MHz, CD$_3$OD) δ 8.37 (s, 1H), 7.89 (dd, J = 1.51, 7.78 Hz, 1H), 7.82 (d, J = 3.76 Hz, 1H), 7.54-7.63 (m, 1H), 7.30 (d, J = 8.28 Hz, 1H), 7.20 (t, J = 7.65 Hz, 1H), 6.81 (s, 1H), 6.78 (d, J = 3.76 Hz, 1H), 5.46 (dt, J = 5.52, 10.67 Hz, 1H), 4.12 (s, 3H), 3.54-3.69 (m, 4H), 2.24-2.44 (m, 4H). MS ESI calculated for C$_{21}$H$_{23}$N$_7$O [M + H]$^+$ 390, found 390. |
| 11 | 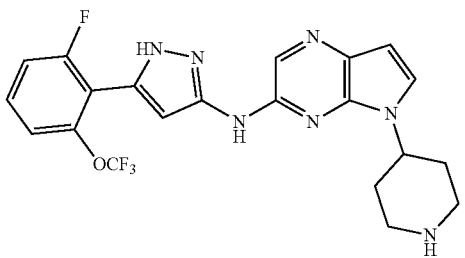 | Compound 11 | Chromatographic column: Venusil ASB Phenyl 250*50 mm 10 μm; mobile phase: [water (0.05% HCl)-acetonitrile]; acetonitrile %: 33%-63%, 10 min. Hydrochloride of compound 11, $^1$H NMR (400 MHz, CD$_3$OD) δ 8.69 (s, 1H), 7.95 (d, J = 3.76 Hz, 1H), 7.64 (dt, J = 6.15, 8.47 Hz, 1H), 7.33-7.44 (m, 2H), 6.74-6.82 (m, 2H), 5.08-5.19 (m, 1H), 3.67 (br d, J = 13.05 Hz, 2H), 3.36 (m, 2H), 2.29-2.47 (m, 4H). MS ESI calculated for C$_{21}$H$_{19}$F$_4$N$_7$O [M + H]$^+$ 462, found 462. |

TABLE 2-continued

| Embo-diment | Starting material | Structural formula | Separation method, ¹HNMR & LCMS |
|---|---|---|---|
| 12 | | Compound 12 | Chromatographic column: Xtimate C18 150*25 mm*5 μm; mobile phase: [water (0.075% TFA)-acetonitrile]; acetonitrile %: 16%-46%, 7 min. Trifluoroacetate of compound 12, ¹H NMR (400 MHz, CD$_3$OD) δ 8.28 (s, 1H), 7.78 (dd, J = 6.5, 8.8 Hz, 1H), 7.58 (d, J = 4.0 Hz, 1H), 7.05-6.98 (m, 1H), 6.86 (dt, J = 2.4, 8.3 Hz, 1H), 6.77 (s, 1H), 6.64 (d, J = 3.8 Hz, 1H), 5.23-5.11 (m, 1H), 4.02 (s, 3H), 3.64 (br d, J = 13.1 Hz, 2H), 3.41-3.34 (m, 2H), 2.45-2.25 (m, 4H). MS ESI calculated for C$_{21}$H$_{22}$FN$_7$O [M + H]$^+$ 408, found 408. |
| 13 | | Compound 13 | Chromatographic column: Xtimate C18 150*25 mm*5 μm; mobile phase: [water (0.075% TFA)-acetonitrile]; acetonitrile %: 22%-36%, 8 min. Trifluoroacetate of compound 13, ¹H NMR (400 MHz, CD$_3$OD) δ 8.27 (s, 1H), 7.66 (d, J = 7.8 Hz, 1H), 7.61 (d, J = 3.8 Hz, 1H), 7.05 (s, 1H), 6.96 (d, J = 7.3 Hz, 1H), 6.78 (s, 1H), 6.66 (d, J = 3.8 Hz, 1H), 5.28-5.19 (m, 1H), 4.02 (s, 3H), 3.64 (br d, J = 12.8 Hz, 2H), 3.41-3.34 (m, 2H), 2.44 (s, 3H), 2.42-2.27 (m, 4H). MS ESI calculated for C$_{22}$H$_{25}$N$_7$O [M + H]$^+$ 404, found 404. |
| 14 | | Compound 14 | Chromatographic column: Venusil ASB Phenyl 250*50 mm 10 μm; mobile phase: [water (0.05% HCl)-acetonitrile]; acetonitrile %: 20%-45%, 10 min. Hydrochloride of compound 14 ¹H NMR (400 MHz, CD$_3$OD) δ 8.43 (s, 1H), 7.77-7.91 (m, 2H), 7.34 (d, J = 1.76 Hz, 1H), 7.21 (dd, J = 1.88, 8.41 Hz, 1H), 6.74-6.90 (m, 2H), 5.32-5.48 (m, 1H), 4.11 (s, 3H), 3.50-3.69 (m, 4H), 2.24-2.52 (m, 4H). MS ESI calculated for C$_{21}$H$_{22}$ClN$_7$O [M + H]$^+$ 424, found 424. |

Embodiment 15

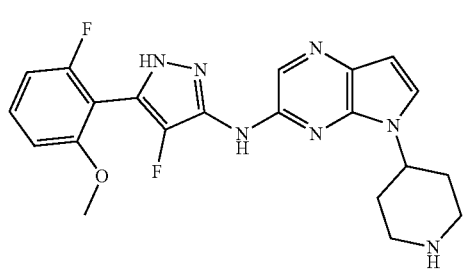

-continued

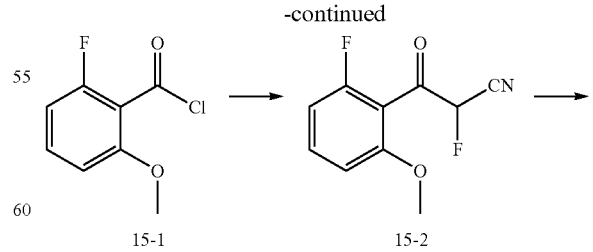

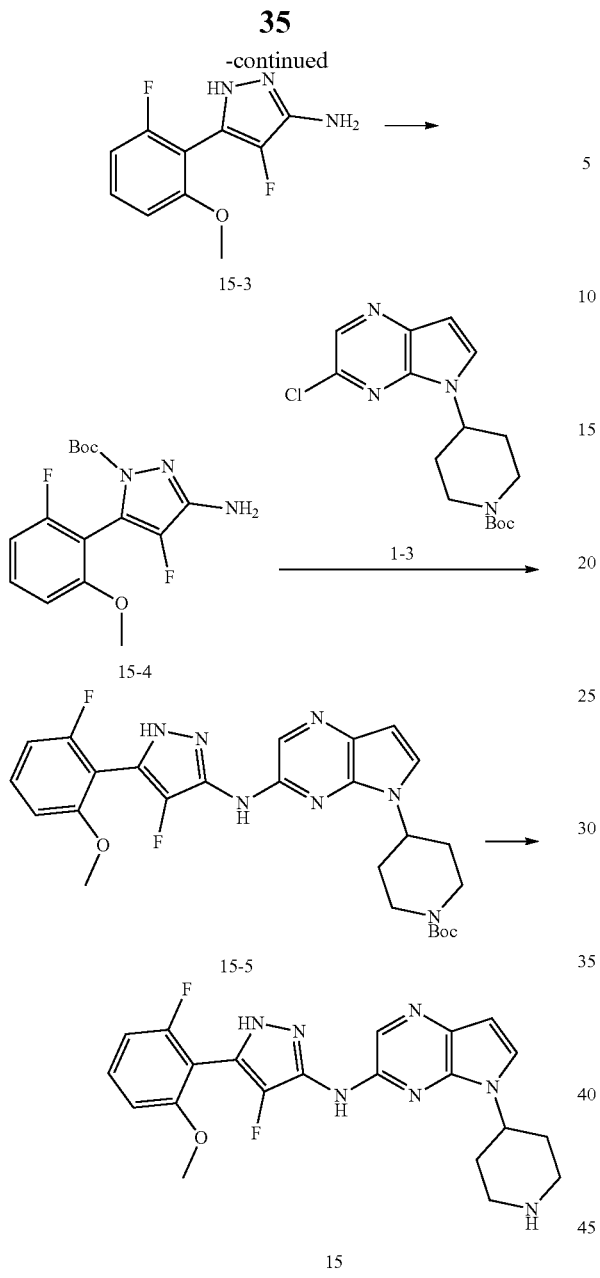

Step 3: Compound 15-3 (200.0 mg, 888.1 μmol) was dissolved in THF (10 mL), then NaH (42.6 mg, 1.07 mmol, 60% purity) was added at 0° C., and after stirred at this temperature for 0.5 hours, di-tert-butyl dicarbonate (232.60 mg, 1.07 mmol) was added, and the reaction solution was stirred at 25° C. for 0.5 hours. After the reaction was finished, water (30 mL) was added, then the mixture was extracted with ethyl acetate (50 mL). The filtrate was concentrated and purified by column chromatography (petroleum ether:ethyl acetate=2:1) to obtain compound 15-4. MS ESI calculated for $C_{15}H_{17}F_2N_3O_3[M+H]^+$ 326, found 326.

Step 4: Compound 15-4 (135.2 mg, 415.7 μmol) and compound 1-3 (140.0 mg, 415.7 μmol) were dissolved in 1,4-dioxane (10 mL), then methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (37.6 mg, 41.5 μmol) and cesium carbonate (270.8 mg, 831.3 μmol) were added successively, and the reaction solution was stirred at 100° C. for 1.5 hours. After the reaction was finished, the mixture was cooled and filtered, and the filtrate was concentrated to obtain a crude product of compound 15-5, which was directly used in the next reaction. MS ESI calculated for $C_{26}H_{29}F_2N_7O_3$ $[M+H]^+$ 526, found 526.

Step 5: Compound 15-5 (100.0 mg, 159.8 μmol) was dissolved in dichloromethane (3 mL), then trifluoroacetic acid (3 mL) was added, and the mixture was stirred at 25° C. for 0.5 hours. After the reaction was finished, the reaction solution was concentrated, and the crude product was separated by preparative high performance liquid chromatography (chromatographic column: Venusil ASB Phenyl 250*50 mm 10 μm; mobile phase: [water (0.05% HCl)-acetonitrile]; acetonitrile %: 20%-50%, 10 min) to obtain the hydrochloride of compound 15. $^1$H NMR (400 MHz, CD$_3$OD) δ 8.61 (s, 1H), 8.08 (d, J=3.8 Hz, 1H), 7.52 (dt, J=6.7, 8.5 Hz, 1H), 7.03 (d, J=8.3 Hz, 1H), 6.92 (t, J=8.9 Hz, 1H), 6.82 (d, J=4.0 Hz, 1H), 5.15-5.03 (m, 1H), 3.93 (s, 3H), 3.71-3.62 (m, 2H), 3.32-3.25 (m, 2H), 2.52-2.35 (m, 4H). MS ESI calculated for $C_{21}H_{21}F_2N_7O$ $[M+H]^+$ 426, found 426.

Embodiment 16

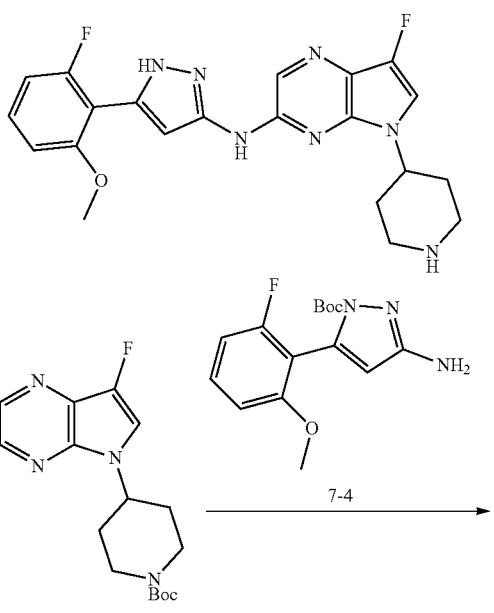

Step 1: 2-Fluoroacetonitrile (353.8 mg, 6.0 mmol) and compound 15-1 (1.0 g, 5.3 mmol) were dissolved in THF (20 mL), then the temperature was lowered to −78° C., and lithium bis(trimethylsilyl)amide(1 M, 11.0 mL) was added dropwise under nitrogen protection and the mixture was stirred at this temperature for 0.5 hours. After the reaction was finished, water (30 mL) was added, then the reaction solution was extracted with ethyl acetate (50 mL). The organic phase was dried and concentrated to obtain a crude product of compound 15-2, which was directly used in the next reaction.

Step 2: Compound 15-2 (1.0 g, 4.7 mmol) and hydrazine hydrate (483.8 mg, 9.5 mmol) were dissolved in EtOH (10 mL) and AcOH (0.1 mL), and the reaction solution was stirred at 100° C. for 2 hours. After the reaction was finished, the reaction solution was concentrated to obtain a crude product of compound 15-3, which was directly used in the next reaction. MS ESI calculated for $C_{10}H_9F_2N_3O$ $[M+H]^+$ 226, found 226.

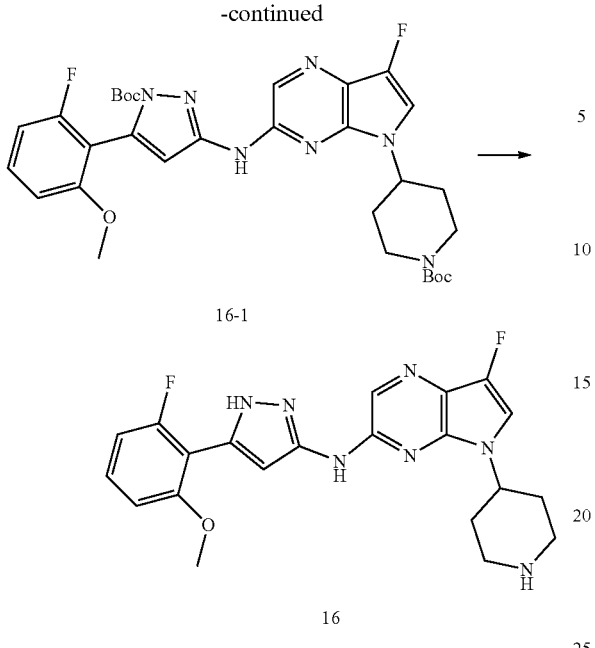

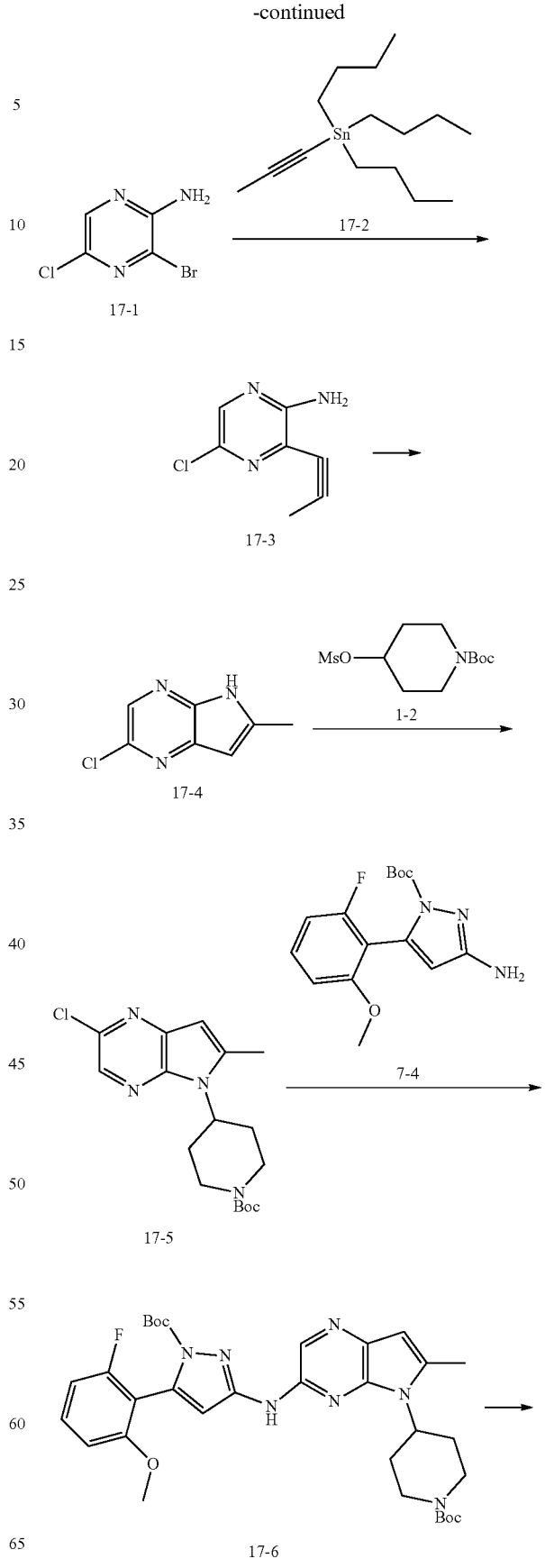

Step 1: Compound 2-2 (110.0 mg, 310.0 μmol) and compound 7-4 (95.3 mg, 310.0 μmol) were dissolved in 1,4-dioxane (10 mL), then methanesulfonato(2-dicyclohexylphosphino-3,6-dimethoxy-2'-4'-6'-tri-i-propyl-1,1'-biphenyl)(2'-amino-1,1'-biphenyl-2-yl)palladium(II) (28.1 mg, 31.0 μmol) and cesium carbonate (202.0 mg, 620.0 μmol) were added successively, and the reaction solution was stirred at 100° C. for 1.5 hours. After the reaction was finished, the mixture was cooled and filtered, and the filtrate was concentrated to obtain compound 16-1. MS ESI calculated for $C_{31}H_{37}F_2N—O_5[M+H]^+$ 626, found 626.

Step 4: Compound 16-1 (50.0 mg, 79.9 μmol) was dissolved in dichloromethane (2 mL), then trifluoroacetic acid (2 mL) was added, and the mixture was stirred at 25° C. for 0.5 hours. After the reaction was finished, the reaction solution was concentrated, and the crude product was separated by preparative high performance liquid chromatography (chromatographic column: Venusil ASB Phenyl 250*50 mm 10 μm; mobile phase: [water (0.05% HCl)-acetonitrile]; acetonitrile %: 25%-55%, 10 min) to obtain the hydrochloride of compound 16. $^1$H NMR (400 MHz, CD$_3$OD) δ 8.28 (s, 1H), 7.66-7.58 (m, 2H), 7.16 (d, J=8.8 Hz, 1H), 7.07-7.00 (m, 1H), 6.90 (s, 1H), 5.51 (br s, 1H), 4.12 (s, 3H), 3.62 (br s, 4H), 2.40-2.20 (m, 4H). MS ESI calculated for $C_{21}H_{21}F_2N_7O$ $[M+H]^+$ 426, found 426.

Embodiment 17

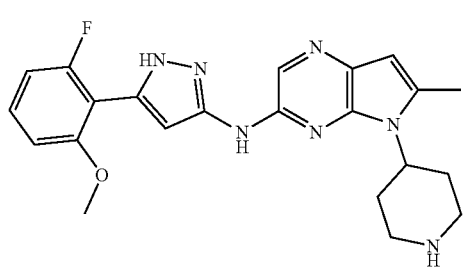

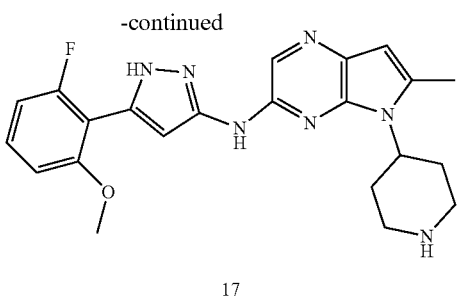

17

Step 1: Compound 17-1 (0.8 g, 3.8 mmol) and compound 17-2 (1.1 g, 3.5 mmol) were added to toluene (2 mL), the CuI (87.7 mg, 460.5 μmol), tetrakis(triphenylphosphine)palladium (310.4 mg, 268.6 μmol) were added successively, and the reaction solution was stirred at 60° C. under nitrogen protection for 12 hours. After the reaction was finished, the reaction solution was filtered. The filtrate was concentrated and purified by column chromatography (petroleum ether:ethyl acetate=1:1) to obtain compound 17-3. MS ESI calculated for $C_7H_6ClN_3$ [M+H]$^+$ 168, found 168.

Step 2: Compound 17-3 (0.4 g, 2.2 mmol) was dissolved in THF (2 mL), and a solution of potassium tert-butoxide in THF (1 M, 3.2 mL) was slowly added dropwise at 0° C. After the dropwise addition was finished, the temperature was raised to 25° C. and the reaction solution was continued to stir for 12 hours. After the reaction was finished, water (2 mL) was added, and the mixture was extracted with ethyl acetate (10 mL). After the organic phase was concentrated, the crude product was purified by column chromatography (petroleum ether:ethyl acetate=2:1) to obtain compound 17-4. $^1$H NMR (400 MHz, CD$_3$OD) δ 8.14 (s, 1H), 6.26 (s, 1H), 2.42 (s, 3H). MS ESI calculated for $C_7H_6ClN$ [M+H]$^+$ 168, found 168.

Step 3: Compound 17-4 (0.2 g, 1.2 mmol) was dissolved in DMF (2 mL), then NaH (95.5 mg, 2.4 mmol, 60% purity) was added, and the mixture was stirred at 25° C. for 0.5 hours, and then 1-2 (1.3 g, 4.8 mmol) was added and then the reaction solution was warmed to 90° C. and stirred for 16 hours. After the reaction was finished, water (5 mL) and ethyl acetate (30 OurRef P22412941US mL) were added for extraction. The organic phase was concentrated and the crude product was purified by column chromatography (petroleum ether:ethyl acetate=3:1) to obtain compound 17-5. MS ESI calculated for $C_{17}H_{23}ClN_4O_2$ [M+H]$^+$ 351, found 351.

Step 4: Compound 17-5 (100.0 mg, 370.5 mg) and compound 7-4 (113.8 mg, 370.5 μmol) were added to anhydrous 1,4-dioxane (2 mL), then methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (33.6 mg, 37.1 μmol) and cesium carbonate (241.4 mg, 741.0 μmol) were added successively, and the reaction solution was stirred at 100° C. for 1 hour.

After the reaction was finished, water (5 mL) and ethyl acetate (30 mL) were added for extraction, and the organic phase was concentrated to obtain a crude product of compound 17-6, which was directly used in the next reaction. MS ESI calculated for $C_{32}H_{40}FN_7O$ [M+H]$^+$ 622, found 622.

Step 5. Compound 17-6 (0.1 g, 160.9 μmol) was dissolved in dichloromethane (2 mL), then trifluoroacetic acid (2 mL) was added, and the mixture was stirred at 25° C. for 5 minutes; after the reaction was finished, the reaction solution was concentrated, and the crude product was separated by preparative high performance liquid chromatography (chromatographic column: Venusil ASB Phenyl 250*50 mm 10 μm; mobile phase: [water (0.05% HCl)-acetonitrile]; acetonitrile %: 20%-50%, 10 min) to obtain the hydrochloride of compound 17. $^1$H NMR (400 MHz, CD$_3$OD) δ ppm 1.11-1.23 (m, 2H) 2.12 (br d, J=15.51 Hz, 2 H) 2.60 (s, 3H) 2.91-3.01 (m, 2H) 3.23-3.30 (m, 2H) 3.55 (br d, J=12.26 Hz, 2H) 3.93 (s, 3H) 6.45 (s, 1H) 6.84 (dd, J=10.94, 8.44 Hz, 1H) 6.95 (d, J=8.38 Hz, 1H) 7.30-7.40 (m, 1H) 8.59 (s, 1H). MS ESI calculated for $C_{22}H_{24}FN_7O$ [M+H]$^+$ 422, found 422.

Embodiment 18

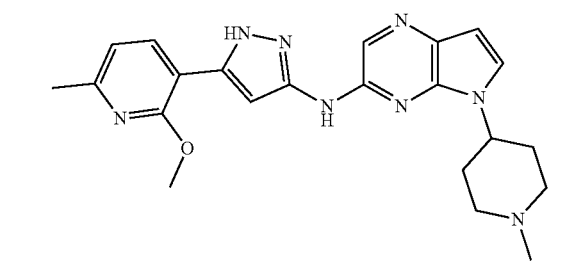

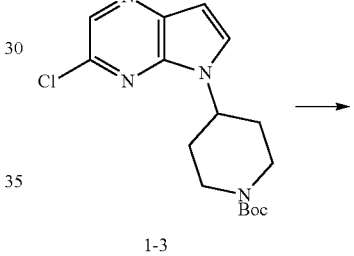

1-3

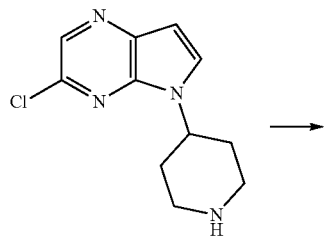

18-1

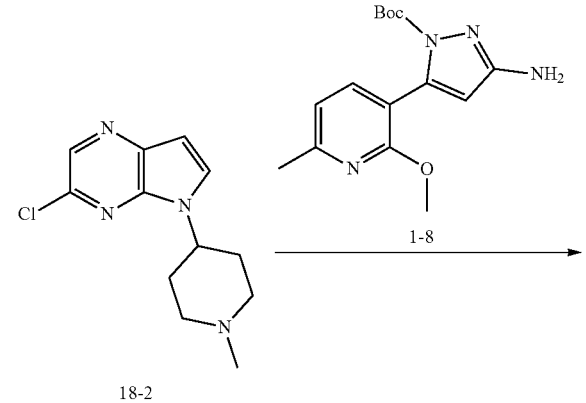

18-2

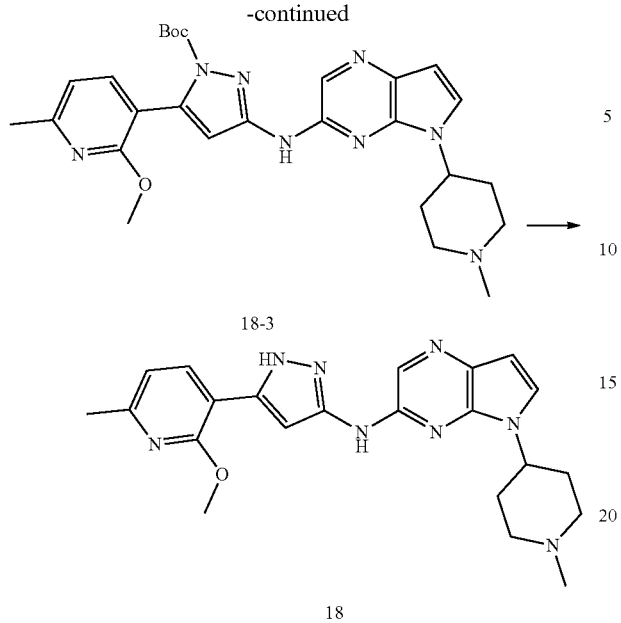

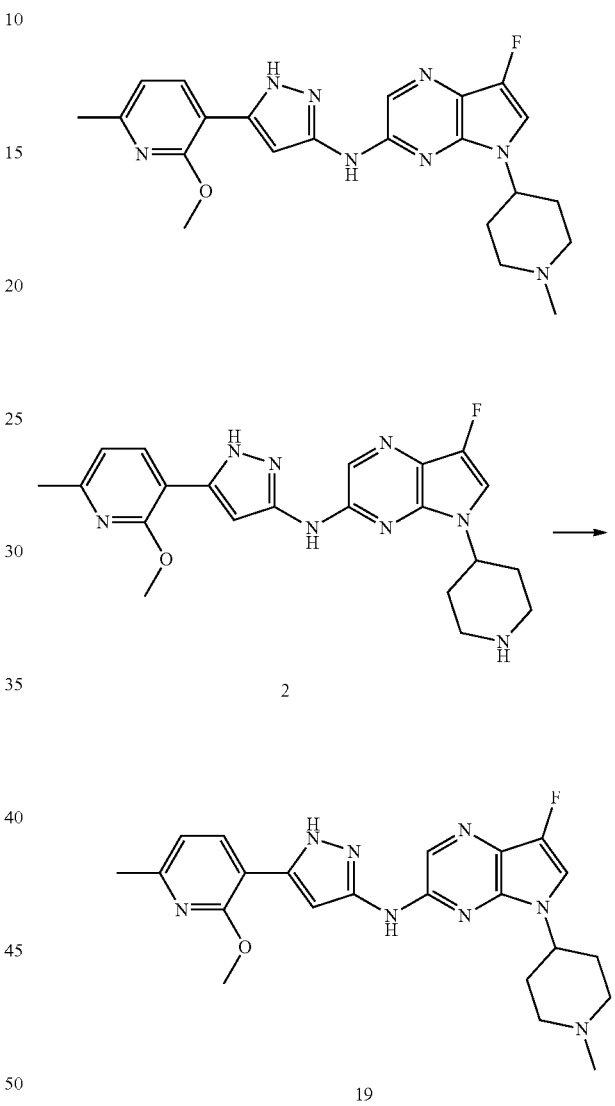

Step 1: Compound 1-3 (150 mg, 0.445 mmol) was dissolved in DCM (20 mL), then HCl/MeOH (4 M, 20 mL) was added, and the reaction solution was stirred at 25° C. for 0.5 hours and then concentrated to obtain a crude product of compound 18-1, which was directly used for the next step. MS ESI calculated for $C_{11}H_{13}ClN_4$ [M+H]⁺ 237, found 237.

Step 2: Compound 18-1 (100 mg, 0.422 mmol) was dissolved in DCM (10 mL) and AcOH (1 mL), then 4A molecular sieves (500 mg) and formaldehyde hydrate (0.314 mL, 4.22 mmol) were added, and the reaction solution was stirred at 25° C. for 0.5 hours, then sodium triacetoxyborohydride (179.08 mg, 0.845 mmol) was added and the reaction solution was continued to stir for 2 hours. After the reaction was finished, the mixture was filtered and concentrated, and the crude product was purified by preparative thin layer chromatography (petroleum ether:ethyl acetate=1:1) to obtain compound 18-2. MS ESI calculated for $C_{12}H_{15}ClN_4$ [M+H]⁺ 251, found 251.

Step 3: Compound 18-2 (85.0 mg, 0.339 mmol) and compound 1-8 (108.2 mg, 0.339 mmol) were dissolved in dioxane (10 mL), then cesium carbonate (165.69 mg, 0.508 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (30.73 mg, 0.034 mmol) were added successively, then the mixture was stirred at 95° C. for 1 hour; after the reaction was finished, the reaction solution was filtered and concentrated to obtain a crude product of compound 18-3, which was directly used in the next reaction. MS ESI calculated for $C_{27}H_{34}N_8O_3$ [M+H]⁺ 519, found 519.

Step 4: Compound 18-3 (80.0 mg, 0.154 mmol) was dissolved in DCM (5 mL), then trifluoroacetic acid (2.0 mL) was added, and the mixture was stirred at 25° C. for 0.5 hours. After the reaction was finished, the reaction solution was concentrated, and the crude product was separated by preparative high performance liquid chromatography (chromatographic column: Boston Green ODS 150*30 mm*5 μm; mobile phase: [water (0.075% TFA)-acetonitrile]; acetonitrile %: 18%-48%, 8 min) to obtain the trifluoroacetate of compound 18. ¹H NMR (400 MHz, CD₃OD) δ 8.32 (s, 1H), 8.03 (d, J=7.50 Hz, 1H), 7.57 (d, J=3.63 Hz, 1H), 6.99 (d, J=7.63 Hz, 1H), 6.80 (s, 1H), 6.64 (d, J=3.63 Hz, 1H), 5.03-5.17 (m, 1H), 4.11 (s, 3H), 3.75 (br d, J=12.38 Hz, 2H), 3.35-3.44 (m, 2H), 3.00 (s, 3H), 2.52 (s, 3H), 2.34-2.47 (m, 4H). MS ESI calculated for $C_{22}H_{26}N_8O$ [M+H]⁺ 419, found 419.

Embodiment 19

Step 1: Compound 2 (4.8 g, 11.3 mmol) was dissolved in methanol (100 mL) and acetic acid (1 mL), then formaldehyde hydrate (1.0 mL, 13.5 mmol, 37% concentration) and sodium cyanoborohydride (850.0 mg, 13.5 mmol) were added, and the reaction solution was stirred at 25° C. for 2 hours. After the reaction was finished, the reaction solution was neutralized with saturated aqueous sodium bicarbonate solution (20 mL) to pH=7; after filtration, the filter cake was washed with water (20 mL), and slurried with acetonitrile (10 mL) to obtain compound 19. ¹H NMR (400 MHz, CD₃OD) δ 8.27 (s, 1H), 7.98 (d, J=7.63 Hz, 1H), 7.32 (d, J=1.38 Hz, 1H), 6.96 (d, J=7.50 Hz, 1H), 6.91 (s, 1H), 4.86-4.80 (brs, 1H), 4.10 (s, 3H), 3.60-3.50 (m, 2H), 3.01-3.21 (m, 2H), 2.84 (s, 3H), 2.51 (s, 3H), 2.33 (brs, 4H). MS ESI calculated for $C_{22}H_{25}FN_8O$ [M+H]⁺ 437, found 437.

Embodiment 20

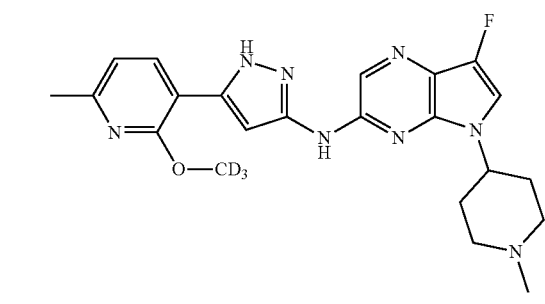

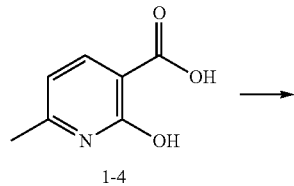

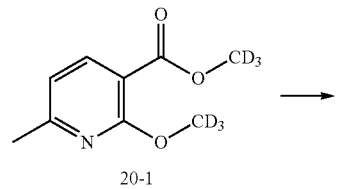

20-1

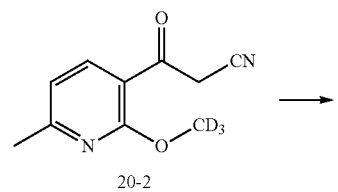

20-2

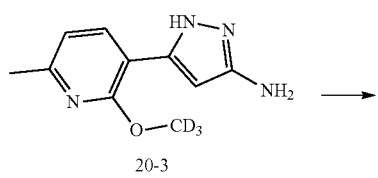

20-3

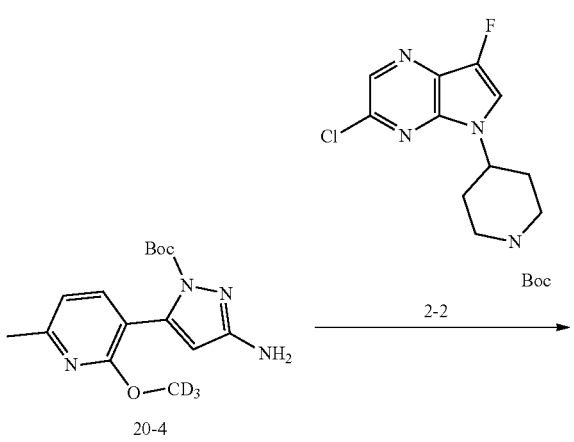

2-2

20-4

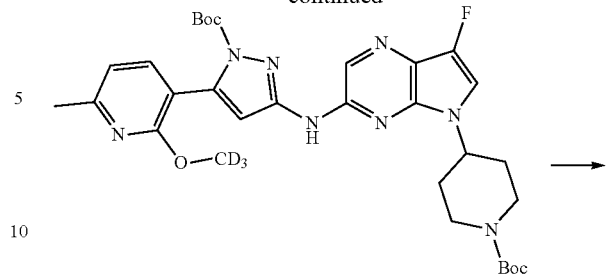

20-5

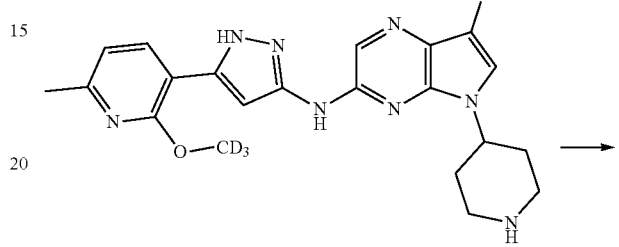

20-6

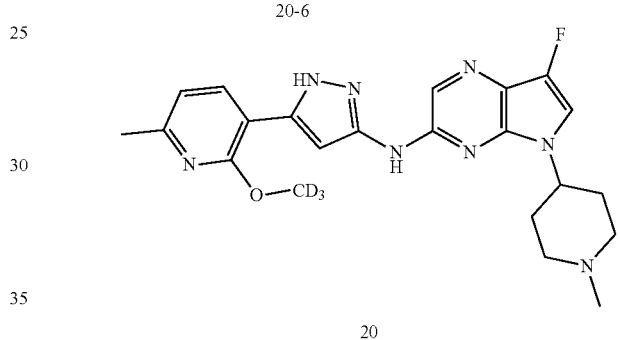

20

Step 1: Compound 1-4 (10.0 g, 65.3 mmol), deuterated iodomethane (21.7 g, 150.2 mmol) were dissolved in chloroform (150 mL), then silver carbonate (19.8 g, 71.8 mmol) was added, and the reaction solution was stirred at 60° C. for 16 hours. After the reaction was finished, the reaction solution was cooled and filtered, and the filtrate was concentrated and the crude product was purified by column chromatography (petroleum ether:ethyl acetate=3:1) to obtain compound 20-1. MS ESI calculated for $C_9H_5D_6NO_3$ [M+H]$^+$ 188, found 188.

Step 2: Acetonitrile (3.0 mL, 57.6 mmol) was added to tetrahydrofuran (100 mL), and n-butyllithium (2.5 M, 24.6 mL, 61.5 mmol) was slowly added dropwise to the reaction solution at −78° C., then the temperature was maintained, and the reaction was carried out for 30 minutes, then compound 20-1 (7.2 g, 38.46 mmol) was slowly added dropwise to the reaction solution; the reaction was continued for 30 minutes, and then the temperature was raised to room temperature, then the reaction solution was poured into water (100 mL), then the mixture was extracted with ethyl acetate (200 mL), concentrated, and the crude product was purified by column chromatography (petroleum ether:ethyl acetate=2:1) to obtain compound 20-2. MS ESI calculated for $C_{10}H_7D_3N_2O_2$ [M+H]$^+$ 194, found 194.

Step 3: Compound 20-2 (7.4 g, 38.4 mmol) was dissolved in ethanol (100 mL), then hydrazine hydrate (4.5 g, 76.9 mmol) and acetic acid (6.6 mL, 115.3 mmol) were added successively, and the reaction solution was stirred at 80° C. for 2 hours; after the reaction was finished, the reaction solution was concentrated, and the crude product was purified by column chromatography (petroleum ether:ethyl acetate=1:1) to obtain compound 20-3. MS ESI calculated for $C_{10}H_9D_3N_4O$ $[M+H]^+$ 208, found 208.

Step 4: Compound 20-3 (7.0 g, 33.7 mmol) was dissolved in tetrahydrofuran (50 mL), then sodium hydride (1.3 g, 33.7 mmol, 60% purity) was added at 0° C. and the mixture was stirred for 0.5 hours, then di-tert-butyl dicarbonate (7.3 g, 33.7 mmol) was added. After the reaction was carried out at 0° C. for 0.5 hours, the reaction solution was concentrated, and the crude product was purified by column chromatography (petroleum ether:ethyl acetate=1:1) to obtain compound 20-4. MS ESI calculated for $C_{15}H_{17}D_3N_4O_3$ $[M+H]^+$ 308, found 308.

Step 5: Compound 20-4 (4.3 g, 14.1 mmol) and compound 2-2 (5.0 g, 14.1 mmol) were dissolved in 1,4-dioxane (150 mL), then cesium carbonate (9.218 g, 28.2 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladium(II)(1.3 g, 1.4 mmol) were added successively, and the reaction solution was stirred at 95° C. for 3 hours. After filtration, the filtrate was concentrated, and the crude product was purified by column chromatography (petroleum ether:ethyl acetate=2:1) to obtain compound 20-5. MS ESI calculated for $C_{31}H_{36}D_3FN_8O_5$ $[M+H]^+$ 626, found 626.

Step 6: Compound 20-5 (8.3 g, 13.2 mmol) was dissolved in dichloromethane (100 mL), then trifluoroacetic acid (10 mL) was added, and the reaction solution was stirred at 25° C. for 0.5 hours; after the reaction was finished, the reaction solution was concentrated and neutralized by saturated aqueous sodium bicarbonate solution to pH=7, then the reaction solution was filtered, washed with water, and the filter cake was slurried with acetonitrile to obtain compound 20-6. MS ESI calculated for $C_{21}H_{20}D_3FN_8O$ $[M+H]^+$ 426, found 426.

Step 7: Compound 20-6 (5.5 g, 12.9 mmol) was dissolved in MeOH (50 mL) and AcOH (1 mL), then formaldehyde hydrate (1.2 mL, 15.5 mmol, 37% concentration) and sodium cyanoborohydride (975.0 mg, 15.5 mmol) were added and the reaction solution was stirred at 25° C. for 2 hours. After the reaction was finished, the reaction solution was neutralized with saturated aqueous sodium bicarbonate solution to pH=7, then the reaction solution was filtered, washed with water (50 mL), and the filter cake was slurried with acetonitrile (10 mL) to obtain compound 20. $^1$H NMR (400 MHz, CD$_3$OD) δ 8.21 (s, 1H), 7.96 (d, J=7.20 Hz, 1H), 7.31 (s, 1H), 7.12 (brs, 1H), 6.93 (d, J=7.53 Hz, 1H), 4.62 (brs, 1H), 3.08 (d, J=11.80 Hz, 2H), 2.50 (s, 3H), 2.39 (s, 3H), 2.33-2.27 (m, 2H), 2.25-2.11 (m, 4H). MS ESI calculated for $C_{22}H_{22}D_3FN_8O$ $[M+H]^+$ 440, found 440.

Embodiment 21

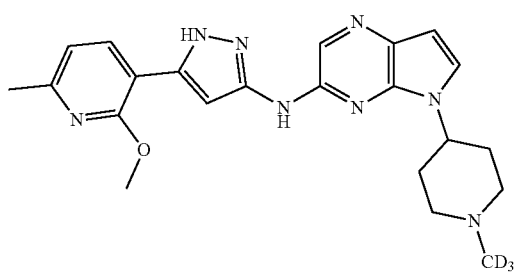

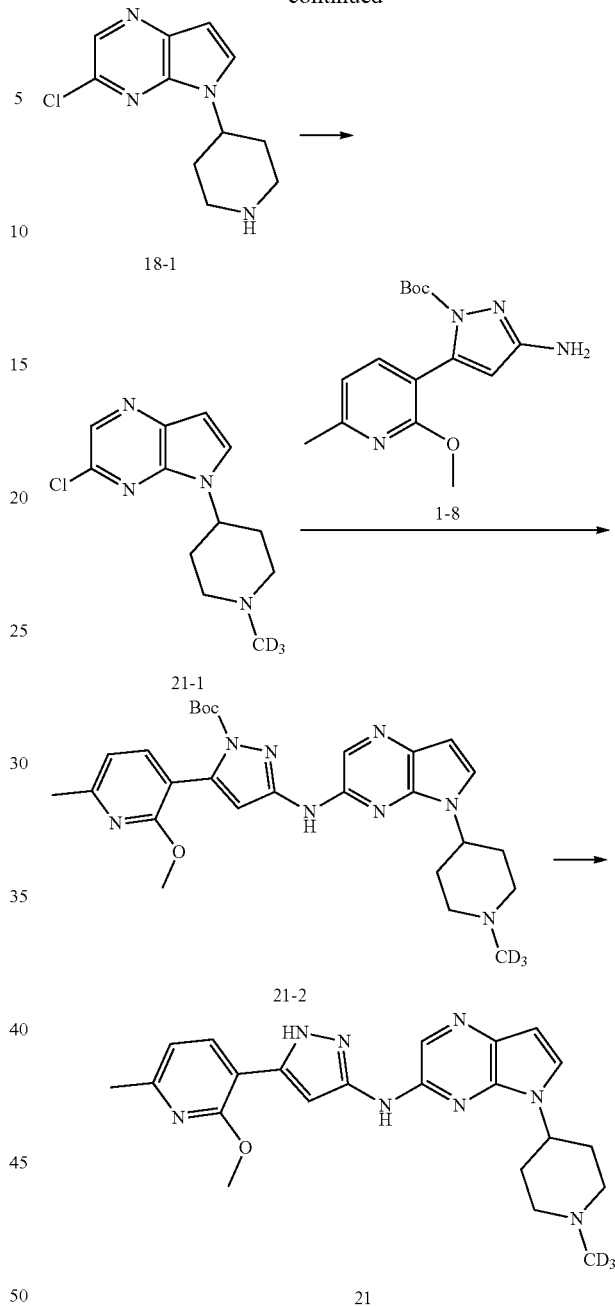

Step 1: Compound 18-1 (1.0 g, 3.6 mmol) was dissolved in DMF (30 mL), then deuterated iodomethane (530.0 mg, 3.6 mmol) and potassium carbonate (1.5 g, 10.9 mmol) were added, and the reaction solution was stirred at 25° C. for 16 hours. After the reaction was finished, the mixture was filtered and concentrated, and the crude product was purified by column chromatography (dichloromethane:methanol=10:1) to obtain compound 21-1. MS ESI calculated for $C_{12}H_{12}D_3ClN_4$ $[M+H]^+$ 254, found 254.

Step 2: Compound 1-8 (100.0 mg, 0.3 mmol) and compound 21-1 (100.0 mg, 0.4 mmol) were dissolved in dioxane (10 mL), then cesium carbonate (214.1 mg, 0.7 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (30.0 mg, 32.0 μmol) were added successively, then the mixture was stirred at 95° C. for 1 hour; the reaction solution was filtered and concentrated to obtain a crude product of compound 21-2, which was directly used in the next reaction. MS ESI calculated for $C_{27}H_{31}D_3N_8O_3$ [M+H]$^+$ 522, found 522.

Step 3: Compound 21-2 (171.0 mg, 0.3 mmol) was dissolved in DCM (10 mL), then trifluoroacetic acid (3.0 mL) was added, and the mixture was stirred at 25° C. for 0.5 hours. After the reaction was finished, the reaction solution was concentrated, and the crude product was separated by preparative high performance liquid chromatography (chromatographic column: Phenomenex Gemini-NX 80*40 mm*3 μm; mobile phase: [water (0.05% ammonia water+10 mM ammonium bicarbonate)-acetonitrile]; acetonitrile %: 27%-57%, 8 min.) to obtain compound 21. $^1$H NMR (400 MHz, CD$_3$OD) δ 8.23 (brs, 1H), 7.98 (d, J=6.78 Hz, 1H), 7.47 (s, 1H), 7.12 (brs, 1H), 6.94 (d, J=7.52 Hz, 1H), 6.51 (d, J=3.02 Hz, 1H), 4.70-4.58 (m, 1H), 4.11 (s, 3H), 3.10 (d, J=10.50 Hz, 2H), 2.50 (s, 3H), 2.37-2.10 (m, 6H). MS ESI calculated for $C_{22}H_{23}D_3N_8O$ [M+H]$^+$ 422, found 422.

Embodiment 22

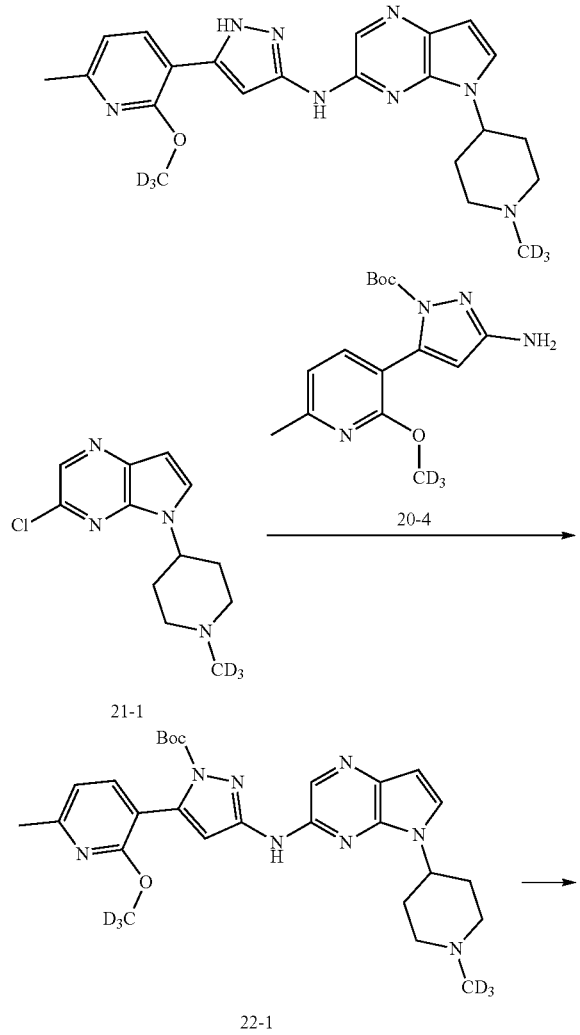

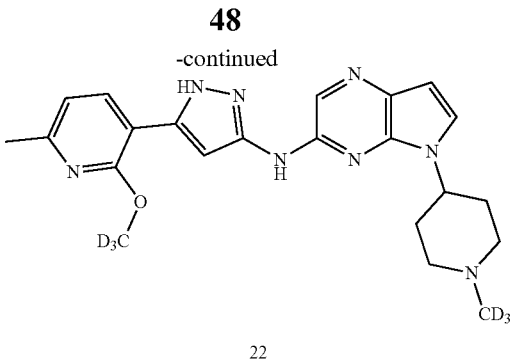

Step 1: Compound 21-1 (100.0 mg, 0.3 mmol) and compound 20-4 (99.0 mg, 0.4 mmol) were dissolved in dioxane (10 mL), then cesium carbonate (214.1 mg, 0.6 mmol) and methanesulfonato(2-dicyclohexylphosphino-3,6-dimethoxy-2'-4'-6'-tri-i-propyl-1,1'-bipheny)(2'-amino-1,1'-biphenyl-2-yl)palladium(II) (30.0 mg, 32.0 μmol) were added successively, and the mixture was stirred at 95° C. for 1 hour; the reaction solution was filtered and concentrated to obtain a crude product of compound 22-1, which was directly used in the next reaction. MS ESI calculated for $C_{27}H_{28}D_6N_8O_3$ [M+H]$^+$ 525, found 525.

Step 2: Compound 22-1 (170.0 mg, 0.3 mmol) was dissolved in DCM (10 mL), then trifluoroacetic acid (3.0 mL) was added, and the mixture was stirred at 25° C. for 0.5 hours. After the reaction was finished, the reaction solution was concentrated, and the crude product was separated by preparative high performance liquid chromatography (chromatographic column: Phenomenex Gemini-NX 80*40 mm*3 μm; mobile phase: [water (0.05% ammonia water+10 mM sodium bicarbonate)-acetonitrile]; acetonitrile %: 27%-57%, 8 min) to obtain compound 22. $^1$H NMR (400 MHz, CD$_3$OD) δ 8.27-8.17 (m, 1H), 8.03-7.94 (m, 1H), 7.50-7.45 (m, 1H), 7.15-7.08 (m, 1H), 6.94 (d, J=7.52 Hz, 1H), 6.51 (brd, J=3.80 Hz, 11H), 4.71-4.58 (m, 1H), 3.11 (brd, J=11.04 Hz, 2H), 2.50 (s, 3H), 2.38-2.11 (m, 6H). MS ESI calculated for $C_{22}H_{20}D_6N_8O$ [M+H]$^+$ 425, found 425.

Experimental Embodiment 1: Activity Test of Compounds in the CHK1 Coupled Reaction System The compounds of the present disclosure used in the experiments were self-prepared, and their chemical names and structural formulas were shown in the preparation embodiments of each compound. The determination mixture containing embodiment compounds of the present disclosure and Chk1 and Chk2 kinases were incubated in a microtiter plate, and CHK1 inhibitor activity of compounds were tested by monitoring the phosphorylation of Chk1 and Chk2 kinases on a synthetic peptide substrate with a specific amino acid sequence (KKKVSRSGLYRSPSMPENLNRPR, SEQ ID NO: 1). The test was carried out on the KinaseProfiler™ protein kinase activity detection platform of Eurofins, and the experimental results were provided by the company. The procedure was as follows: Chk1 and Chk2 kinases were diluted with 20 mM MOPS (morpholinpropane sulfonic acid), 1 mM EDTA (ethylenediaminetetraacetic acid), 0.04% Brij-35, 5% glycerol, 0.1% 2-mercaptoethanol, 1 mg/mL BSA (bovine serum albumin) and added to the reaction system, and the reaction system contained the embodiment compounds, 8 mM MOPS pH 7.0, 0.2 mM EDTA, 200 sM polypeptide substrate (KKKVSRSGLYR-SPSMPENLNRPR, SEQ ID NO: 1), 10 mM magnesium acetate and a certain concentration of [γ-33P]-ATP (the strength was about 500 cpm/pmol). A mixture solution of $Mg^{2+}$ and ATP (adenosine triphosphate) was added to initiate the reaction and the reaction solution was incubated at room temperature for 40 min. 0.5% Phosphate buffer was added to terminate the reaction. 10 μL of the reaction solution was filtered four times on a continuous filter P30, washed three times with 0.425 phosphate buffer, and once with methanol, each wash for 4 min. The value was read with scintillation counting method after drying.

The compound inhibitory activity results were shown in Table 3.

Table 3. Inhibitory activity results of the compound on Chk1/Chk2 enzyme

TABLE 3

Inhibitory activity results of the compound on Chk1/Chk2 enzyme

| Compound | Chk1 inhibition $IC_{50}$ (nM) | Chk2 inhibition $IC_{50}$ (nM) |
|---|---|---|
| 1 | <1 | 79 |
| Trifluoroacetate of 2 | 2 | 28 |
| Trifluoroacetate of 3 | 5 | 1966 |
| Trifluoroacetate of 4 | 3 | 333 |
| Trifluoroacetate of 5 | 3 | 375 |
| 6 | <1 | 64 |
| 7 | 1 | 13 |
| Trifluoroacetate of 8 | 1 | 188 |
| Trifluoroacetate of 9 | 2 | 1011 |
| Hydrochloride of 10 | 2 | 62 |
| Hydrochloride of 11 | 3 | 99 |
| Trifluoroacetate of 12 | 1 | 32 |
| Trifluoroacetate of 13 | 2 | 84 |
| Hydrochloride of 14 | 1 | 73 |
| Hydrochloride of 15 | 2 | 24 |
| Hydrochloride of 16 | <1 | 2 |
| Hydrochloride of 17 | 1 | 43 |
| Trifluoroacetate of 18 | <1 | 257 |
| 19 | 2 | 166 |
| 20 | 2 | 282 |
| 21 | 1 | 362 |
| 22 | 1 | 386 |

Experimental Conclusions:

The compound of the present disclosure exhibits good Chk1 inhibitory activity, and has potential application value for the treatment of Chk1-related diseases (such as cell proliferation-related diseases).

Experimental Embodiment 2: Pharmacokinetic Evaluation of Compounds

Experimental Purpose: To Test the Pharmacokinetics of the Compounds in Mice

Experimental Materials:

C57BU/6 mice (female, 7-9 weeks old, Shanghai Slack)

Experimental operation: The clear solution obtained after the test compound was dissolved was injected into female C57BL/6 mice by tail vein injection and gavage respectively (overnight fasted, 7-9 weeks old). After administration of test compound or control compound, the dose of intravenous injection group was 1 mg/kg, at 0.0833, 0.25, 0.5, 1, 2, 4, 6, 8 and 24 hours, and the dose of gavage group was 10 mg/kg, at 0.0833, 0.25, 0.5, 1, 2, 4, 6, 8, and 24 hours, blood was collected from the mandibular vein and centrifuged to obtain plasma. The plasma concentration was determined by LC-MS/MS method, and the relevant pharmacokinetic parameters were calculated by the non-compartmental model linear logarithmic trapezoid method using WinNonlin™ Version 6.3 pharmacokinetic software. The test results were shown in Table 4:

TABLE 4

PK test results of compounds in mice

| PK parameter | Compound 18 | Compound 19 | Compound 20 |
|---|---|---|---|
| Intravenous injection $T_{1/2}$ (h) | 0.9 | 1.1 | 1.4 |
| Vd (L/kg) | 1.9 | 2.4 | 2.7 |
| Cl (mL/min/kg) | 35.3 | 33.1 | 30.9 |
| Intravenous Injection $AUC_{0\text{-}last}$ (nM · hr) | 1138 | 1148 | 1212 |
| $C_{max}$ (nM) | 1223 | 1215 | 1255 |
| Oral $AUC_{0\text{-}last}$ (nM · hr) | 3629 | 3912 | 5135 |
| F (%) | 33.2 | 39.1 | 41.9 |

Note:
$T_{1/2}$: half-life;
$C_{max}$: peak concentration;
Vd (L/kg): apparent volume of distribution;
Cl (mL/min/kg): clearance rate;
$AUC_{0\text{-}last}$: the area under the plasma concentration-time curve from time 0 to 24 h;
F: bioavailability.

Conclusion: The compounds of the present disclosure have good oral bioavailability and high exposure, which is beneficial to produce good efficacy in vivo.

Experimental Embodiment 3 In Vivo Pharmacodynamics Study of Human Ovarian Cancer OVCAR-3 Subcutaneous Xenograft Tumor BALB/c Nude Mouse Model Experimental purpose: To evaluate the in vivo efficacy of the compounds of the present disclosure in the human ovarian cancer OVCAR-3 subcutaneous xenograft tumor BALB/c nude mouse model.

Experimental animal: Female BALB/c nude mice, 6-8 weeks old, weighing 18-22 grams; supplier: Beijing Vital River Laboratory Animal Technology Co., Ltd. Experimental methods and steps:

3.1 Cell Culture

Human ovarian cancer OVCAR-3 (ATCC-HTB-161) cells were cultured in vitro in monolayer, and the culture conditions were RPMI1640 culture medium with 20% fetal bovine serum, 0.01 mg/mL bovine insulin, and 1% double antibody, and the cells were incubated at 37° C., 5% $CO_2$ incubator. Routine digestion with trypsin was performed twice a week for passage. When the cell saturation was 80%-90% and the number reached the requirement, the cells were harvested, counted and inoculated.

3.2 Tumor Cell Inoculated (Tumor Inoculated)

0.1 mL ($10 \times 10^6$ cells) of OVCAR-3 cells were subcutaneously inoculated into the right back of each mouse, and the mice were administrated in groups when the average tumor volume reached 122 mm³.

3.3 Preparation of Test Substances

Compound 18, compound 19 were formulated as 2 mg/mL clear solutions with 10% dimethyl sulfoxide-20% polyethylene glycol 400-5% Tween 80-65% water.

3.4 Tumor Measurement and Experimental Indicators

Tumor diameters were measured with vernier calipers twice a week. The calculation formula of tumor volume was. V=0.5a×b², where a and b represented the long and short diameters of the tumor, respectively.

The antitumor efficacy of the compounds was evaluated by TGI (%). TGI (%), reflecting tumor growth inhibition rate. TGI (%/c)=[(1-(average tumor volume at the end of administration of a certain treatment group-average tumor volume at the beginning of administration of this treatment group)/(average tumor volume at the end of treatment in the solvent control group-average tumor volume at the beginning of administration of this solvent control group)]×100%. The relative tumor volume (RTV) was calculated according to the results of tumor measurement, and the calculation formula was RTV=$V_t/V_0$, where $V_0$ was measured at the time of group administration (i.e., $D_0$), and $V_t$ was the average tumor volume at the time of one measurement.

3.5 Statistical Analysis

Statistical analysis was performed using SPSS software based on RTV data at the end of the test. The $T_{test}$ was used for the comparison between two groups, and the one-way ANOVA was used for the comparison between three or more groups. If the variance was homogeneous (no significant difference in F value), Tukey's method was used for analysis; if the variance was not homogeneous (significant difference in F value), Games-Howell method was used for test. p<0.05 was considered that a significant difference was performed.

3.6 Test Results

The human ovarian cancer OVCAR-3 subcutaneous xenograft tumor BALB/c nude mice were treated with embodiment 18, embodiment 19 respectively, and the tumor volume changes in each group after the treatment were shown in Table 5.

TABLE 5

Inhibitory effect of embodiment compounds on OVCAR-3 xenograft tumor model

| Group | Tumor volume (mm$^3$)$^a$ (D 0) | Tumor volume (mm$^3$)$^a$ (D 21) | RTV (D 21) | TGI (%) (D 21) | p-value$^b$ |
|---|---|---|---|---|---|
| Vehicle control group | 122 ± 12 | 885 ± 159 | 7.32 | — | — |
| Compound 18$^c$ | 122 ± 12 | 180 ± 16 | 1.49 | 92.34 | 0.024 |
| Compound 19$^d$ | 122 ± 14 | 131 ± 12 | 1.14 | 98.76 | 0.018 |

Note:
$^a$Mean ± SEM, n = 6.
D 0: On the day of administration in groups,
D 21: the 21 st day of administration;

b. the p value of the relative tumor volume (RTV) of the administration group compared with the vehicle control group was obtained by using one-way ANOVA to analyze the tumor volume. Due to variance was not homogeneous (the F value was significantly different), the Games-Howell method was used for post-hoc test. p<0.05 was considered that a significant difference was performed.

c. Oral, 75 mg/kg, twice a day, on the 0th to 10th days, administrated for 3 days and stopped for 4 days, and continued to administrate on the 11th to 21st days.

d. Oral, 25 mg/kg, twice a day, on the 0th to 10th days, administrated for 3 days and stopped for 4 days, and continued to administrate on the 11th to 21st days.

"-" there was not need to calculate.

3.7 Test Conclusions and Discussion

In the OVCAR-3 human ovarian cancer xenograft tumor model, 21 days after the start of administration, the average tumor volume of tumor-bearing mice in the vehicle control group reached 885 mm$^3$, and the TGI of compound 18 was 92.3% compared with the vehicle control group (p=0.024), and the mean tumor volume was 180 mm$^3$. Compound 19 had a TGI of 98.8% (p=0.01$^8$) compared with the vehicle control group, and the mean tumor volume was 131 mm$^3$. The above results show that the embodiment compounds of the present disclosure have significant antitumor efficacy in the human OVCAR-3 human ovarian cancer xenograft tumor model.

What is claimed is:

1. A compound represented by formula (I) or a pharmaceutically acceptable salt thereof,

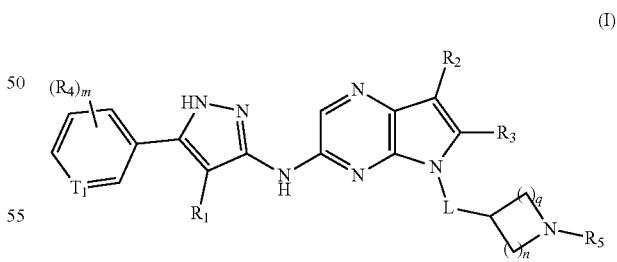

wherein,
$T_1$ is selected from CH and N;
L is selected from a single bond and —$CH_2$—;
m is selected from 0, 1, 2, 3 and 4;
each of n and q is independently selected from 1 and 2;
$R_1$ is selected from H, F, Cl, Br and I;
$R_2$ is selected from H, D, F, Cl, Br and I;
$R_3$ is selected from H, F, Cl, Br, I, CN and $C_{1-3}$ alkyl, and the $C_{1-3}$ alkyl is optionally substituted by 1, 2 or 3 $R_a$;

each of $R_4$ is independently selected from H, F, Cl, Br, I, $C_{1-3}$ alkyl and $C_{1-3}$ alkoxy, and the $C_{1-3}$ alkyl and $C_{1-3}$ alkoxy are optionally substituted by 1, 2 or 3 $R_b$;

$R_5$ is selected from H and $C_{1-3}$ alkyl, and the $C_{1-3}$ alkyl is optionally substituted by 1, 2 or 3 $R_c$;

each of $R_a$, $R_b$ and $R_c$ is independently selected from H, D, F, Cl, Br and I.

2. The compound or the pharmaceutically acceptable salt thereof as claimed in claim 1, wherein, the $R_1$ is selected from H and F.

3. The compound or the pharmaceutically acceptable salt thereof as claimed in claim 1, wherein, the $R_3$ is selected from H and $CH_3$.

4. The compound or the pharmaceutically acceptable salt thereof as claimed in claim 1, wherein, each of the $R_4$ is independently selected from H, F, Cl, $CH_3$ and $OCH_3$, and the $CH_3$ and $OCH_3$ are optionally substituted by 1, 2 or 3 $R_b$.

5. The compound or the pharmaceutically acceptable salt thereof as claimed in claim 1, wherein, each of the $R_4$ is independently selected from H, F, Cl, $CH_3$, $CF_3$, $OCH_3$, $OCD_3$ and $OCF_3$.

6. The compound or the pharmaceutically acceptable salt thereof as claimed in claim 1, wherein, the structural moiety

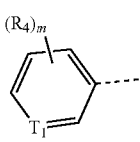

is selected from

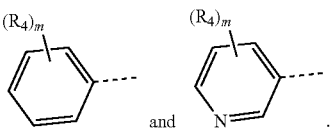

7. The compound or the pharmaceutically acceptable salt thereof as claimed in claim 6, wherein, the structural moiety

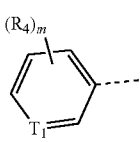

is selected from

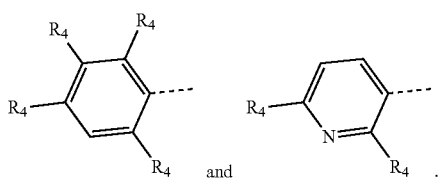

8. The compound or the pharmaceutically acceptable salt thereof as claimed in claim 7, wherein, the structural moiety

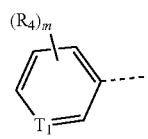

is selected from

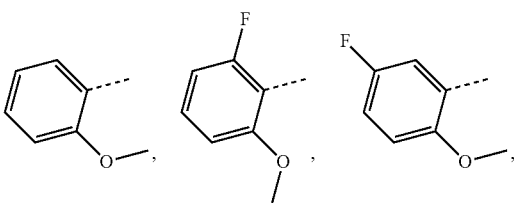

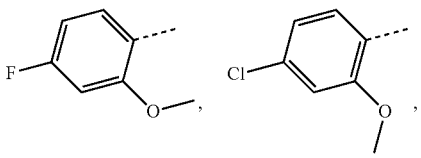

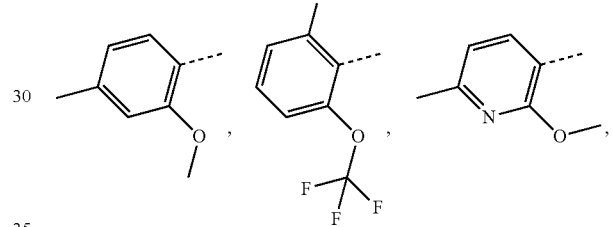

9. The compound or the pharmaceutically acceptable salt thereof as claimed in claim 1, wherein, the $R_5$ is selected from H, $CH_3$ and $CD_3$.

10. The compound or the pharmaceutically acceptable salt thereof as claimed in claim 1, wherein, the structural moiety

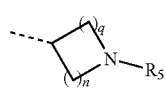

is selected from

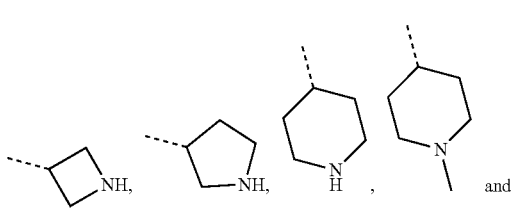

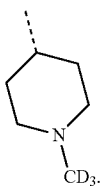

11. The compound or the pharmaceutically acceptable salt thereof as claimed in claim 10, wherein, the structural moiety

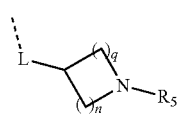

is selected from

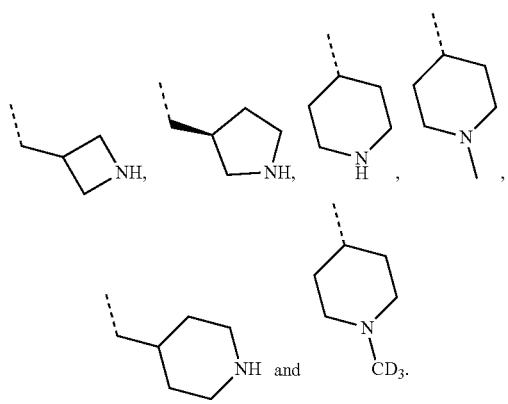

12. The compound or the pharmaceutically acceptable salt thereof as claimed in claim 1, wherein the compound is selected from

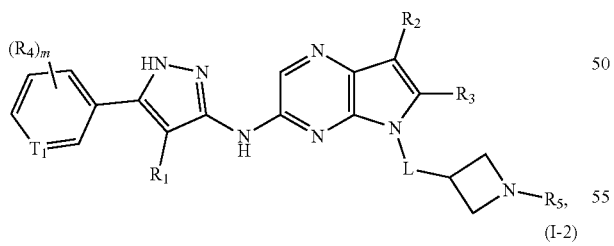

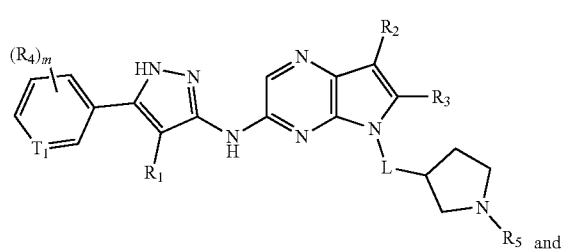

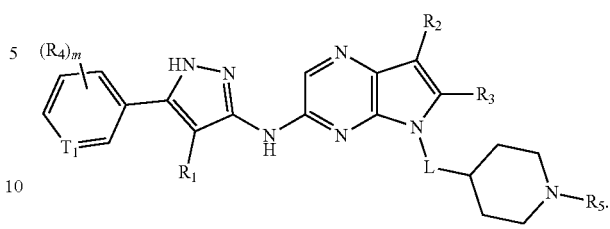

13. A compound represented by the following formula or a pharmaceutically acceptable salt thereof, wherein the compound is selected from

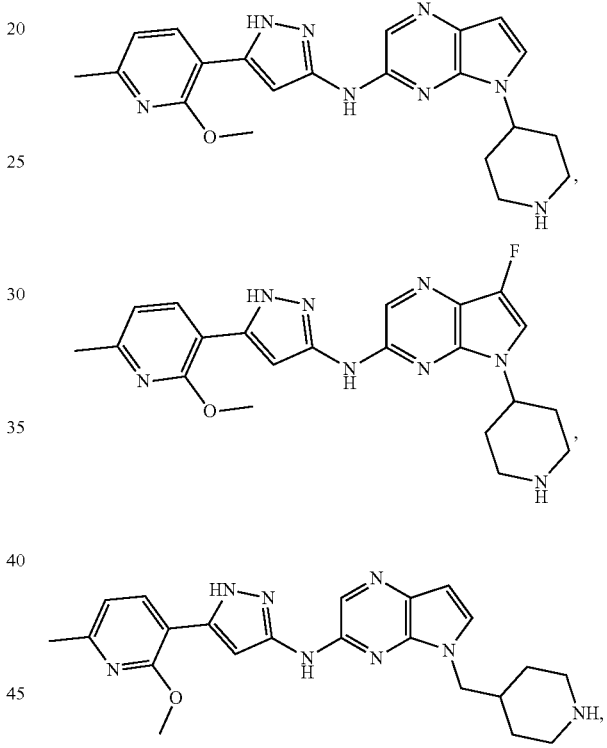

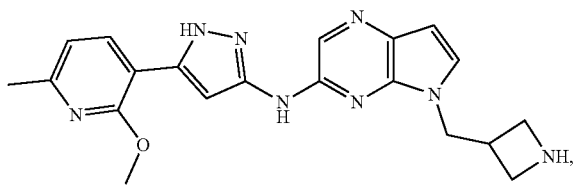

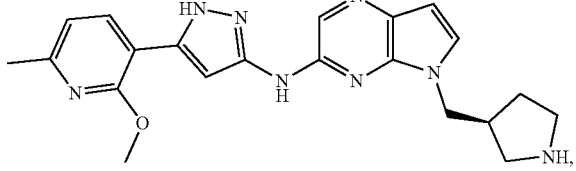

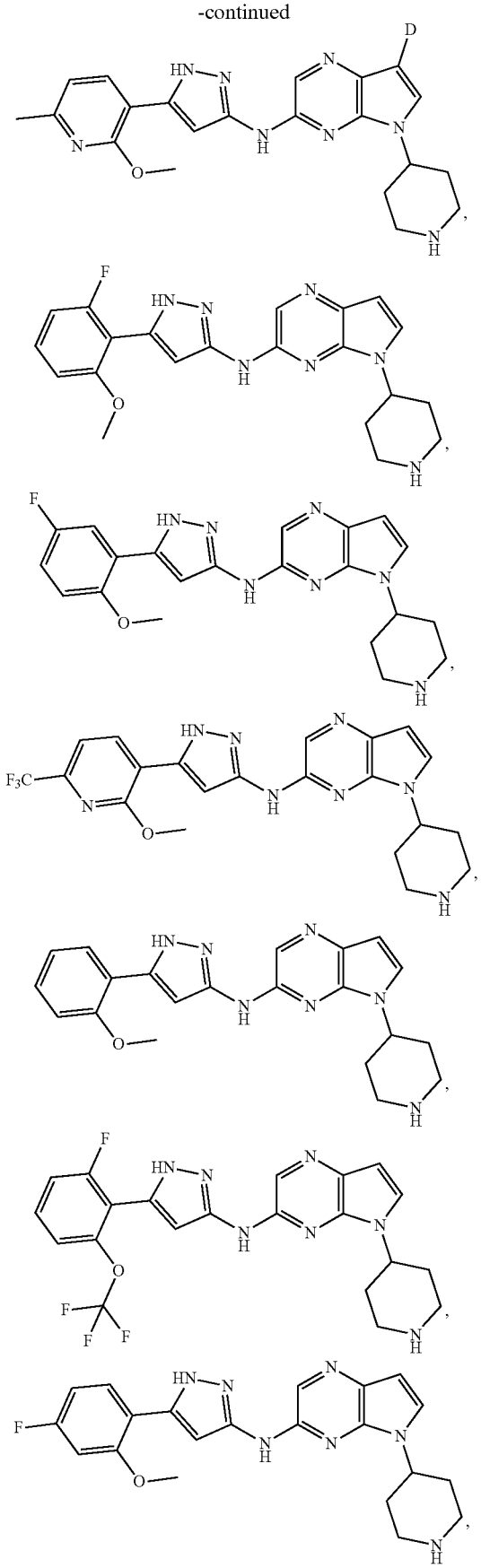
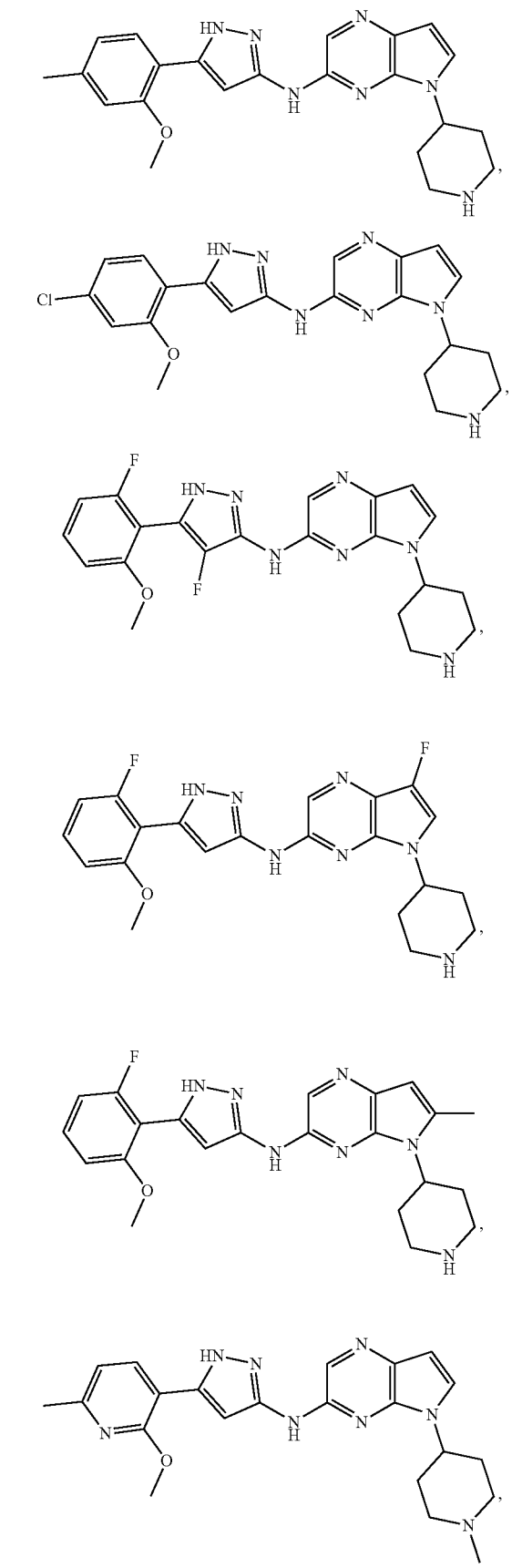

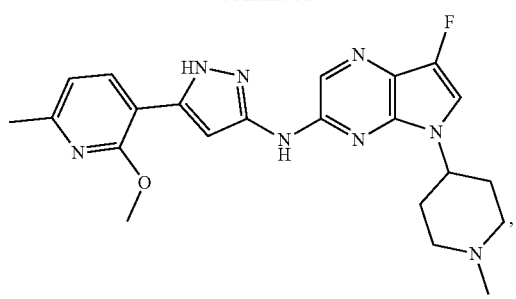
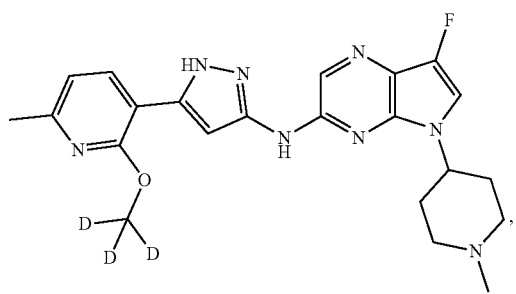
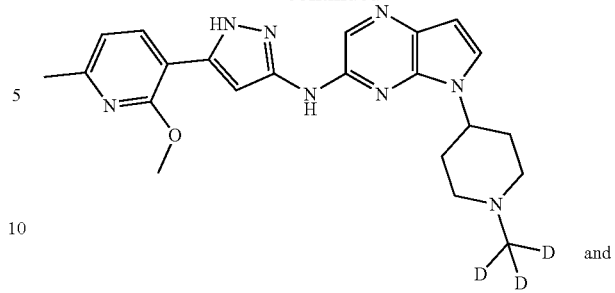
* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: synthetic peptide substrate

<400> SEQUENCE: 1

Lys Lys Lys Val Ser Arg Ser Gly Leu Tyr Arg Ser Pro Ser Met Pro
1               5                   10                  15

Glu Asn Leu Asn Arg Pro Arg
            20
```